(12) United States Patent
Bédard

(10) Patent No.: US 7,147,667 B2
(45) Date of Patent: Dec. 12, 2006

(54) CONTROL SYSTEM AND METHOD FOR CONTROLLING AN ACTUATED PROSTHESIS

(75) Inventor: Stéphane Bédard, Saint-Augustin-de-Desmaures (CA)

(73) Assignee: Victhom Human Bionics Inc., Quebec (CA)

( * ) Notice: Subject to any disclaimer, the term of this patent is extended or adjusted under 35 U.S.C. 154(b) by 211 days.

(21) Appl. No.: 10/600,725

(22) Filed: Jun. 20, 2003

(65) Prior Publication Data
US 2004/0049290 A1 Mar. 11, 2004

Related U.S. Application Data

(60) Provisional application No. 60/453,556, filed on Mar. 11, 2003, provisional application No. 60/424,261, filed on Nov. 6, 2002, provisional application No. 60/405,281, filed on Aug. 22, 2002.

(51) Int. Cl.
*A61F 2/70* (2006.01)
(52) U.S. Cl. .................................................. 623/24
(58) Field of Classification Search ............... 623/24; 700/253, 262, 263
See application file for complete search history.

(56) References Cited

U.S. PATENT DOCUMENTS

| | | | |
|---|---|---|---|
| 4,030,141 A | 6/1977 | Graupe | |
| 4,521,924 A | 6/1985 | Jacobsen et al. | |
| 5,062,856 A | 11/1991 | Sawamura et al. | |
| 5,252,102 A | 10/1993 | Singer et al. | |
| 5,383,939 A | 1/1995 | James | |
| 5,443,528 A | 8/1995 | Allen | |
| 5,571,205 A | 11/1996 | James | |
| 5,571,213 A | 11/1996 | Allen | |
| 5,650,704 A | 7/1997 | Pratt et al. | |
| 5,704,946 A | 1/1998 | Greene | |
| 5,779,735 A | 7/1998 | Molino | |
| 5,888,212 A | 3/1999 | Petrofsky et al. | |
| 5,888,213 A | 3/1999 | Sears et al. | |
| 5,888,246 A | 3/1999 | Gow | |

(Continued)

FOREIGN PATENT DOCUMENTS

FR 2623086 5/1989

(Continued)

OTHER PUBLICATIONS

EPO—International Search Report, Nov. 20, 2003 : PCT/CA03/00937.

*Primary Examiner*—David H. Willse
(74) *Attorney, Agent, or Firm*—Paul C. Remus; Devine, Millimet & Branch

(57) ABSTRACT

The method and the control system are used for determining a portion of locomotion and a phase of locomotion portion in view of controlling an actuated prosthesis in real time. Accordingly, the method comprises receiving a data signal from a plurality of main artificial proprioceptors, obtaining a first and a second derivative signal for each data signal, obtaining a third derivative signal for at least one of the data signals, using a set of a first state machines to select one state among a plurality of possible states for each artificial proprioceptor with the corresponding data and derivative signals, generating the phase of locomotion portion using the states of the main artificial proprioceptors; and using a second state machine to select the portion of locomotion among a plurality of possible portions of locomotion using events associated to the data signals. It is particularly well adapted for the control of an actuated leg prosthesis for above-knee amputees.

40 Claims, 20 Drawing Sheets

U.S. PATENT DOCUMENTS

| | | |
|---|---|---|
| 5,893,891 A | 4/1999 | Zahedi |
| 6,007,582 A | 12/1999 | May |
| 6,113,642 A | 9/2000 | Petrofsky et al. |
| 6,361,570 B1 | 3/2002 | Gow |
| 6,494,039 B1 | 12/2002 | Pratt et al. |
| 2001/0029400 A1 | 10/2001 | Deffenbaugh et al. |
| 2002/0052663 A1 | 5/2002 | Herr et al. |

FOREIGN PATENT DOCUMENTS

| | | |
|---|---|---|
| JP | 11056885 A | 3/1999 |
| JP | 2001277175 A | 10/2001 |
| WO | WO 01/72245 | 10/2001 |

CONTROL SYSTEM AND METHOD FOR CONTROLLING AN ACTUATED PROSTHESIS

CROSS-REFERENCE TO RELATED APPLICATIONS

The present application claims the benefit of U.S. provisional patent applications No. 60/405,281 filed Aug. 22, 2002; No. 60/424,261 filed Nov. 6, 2002; and No. 60/453,556 filed Mar. 11, 2003, all of which are hereby incorporated by reference.

TECHNICAL FIELD

The present invention relates to a control system and a method for controlling an actuated prosthesis. This invention is particularly well adapted for controlling an actuated leg prosthesis for above-knee amputees.

BACKGROUND OF THE INVENTION

As is well known to control engineers, the automation of complex mechanical systems is not something easy to achieve. Among such systems, conventional powered artificial limbs, or myoelectric prostheses, as they are more commonly referred to, are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless of the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional myoelectric prostheses do not have the capability to interact simultaneously with the human body and the external environment in order to have minimal appropriate functioning.

For example, in the case of artificial leg prostheses for above-knee amputees, the complexity of human locomotion resulted in that the technical improvements of conventional leg prostheses have until now been focused on passive mechanisms. This proved to be truly detrimental to the integration of motorized leg prostheses onto the human body. According to amputees, specific conditions of use of conventional leg prostheses, such as repetitive movements and continuous loading, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

The major problem remains that the energy used during mobility mainly stems from the user because conventional leg prostheses are not equipped with servomechanisms that enable self-propulsion. This energy compensation has considerable short and long-term negative effects resulting from the daily use of such prostheses. Accordingly, the dynamic role played by the stump during locomotion renders impossible the prolonged wearing of the prostheses as it may create, among other things, several skin problems such as folliculitis, contact dermatitis, edema, cysts, skin shearing, scarring and ulcers. Although these skin problems may be partially alleviated by using a silicone sheath, a complete suction socket, or powder, skin problems remain one of the major preoccupations today.

As well, the passive nature of the conventional leg prostheses typically leads to movement instability, disrupted movement synchronism and reduced speed of locomotion. Recent developments in the field of energy-saving prosthetic components have partially contributed to improve energy transfer between the amputee and the prosthesis. Nevertheless, the problem of energy expenditure is still not fully resolved and remains the major concern.

Considering this background, it clearly appears that there was a need to develop an improved control system and a new method for controlling an actuated prosthesis in order to fulfill the needs of amputees, in particular those of above-knee amputees.

SUMMARY OF THE INVENTION

In accordance with one aspect of the present invention, there is provided a method for determining a portion of locomotion and a phase of locomotion portion in view of controlling an actuated prosthesis in real time, the method comprising:

providing a plurality of main artificial proprioceptors;

receiving a data signal from each of the main artificial proprioceptors;

obtaining a first and a second derivative signal for each data signal;

obtaining a third derivative signal for at least one of the data signals;

using a set of a first state machines to select one state among a plurality of possible states for each main artificial proprioceptor with the corresponding data and derivative signals;

generating the phase of locomotion portion using the states of the main artificial proprioceptors; and using a second state machine to select the portion of locomotion among a plurality of possible portions of locomotion using events associated to the data signals.

In accordance with another aspect of the present invention, there is provided a method for controlling an actuated prosthesis in real time, the method comprising:

providing a plurality of main artificial proprioceptors;

receiving a data signal from each of the main artificial proprioceptors;

obtaining a first and a second derivative signal for each data signal;

obtaining a third derivative signal for at least one of the data signals;

using a set of first state machines to select one state among a plurality of possible states for each main artificial proprioceptor with the corresponding data and derivative signals;

generating the phase of locomotion portion using the states of the main artificial proprioceptors;

using a second state machine to select the portion of locomotion among a plurality of possible portions of locomotion using events associated to the data signals;

calculating a locomotion speed value;

determining coefficient values from a lookup table using at least the phase of locomotion portion, the portion of locomotion and the locomotion speed value;

calculating at least one dynamic parameter value of the actuated prosthesis using the coefficient values from the lookup table; and converting the dynamic parameter value into an output signal to control the actuated prosthesis.

In accordance with a further aspect of the present invention, there is provided a device for determining a portion of locomotion and a phase of locomotion portion in view of controlling an actuated prosthesis in real time using a plurality of main artificial proprioceptors, the device comprising:

a data signal input for each of the main artificial proprioceptors;

means for obtaining a first and a second derivative signal for each data signal;

means for obtaining a third derivative signal for at least one of the data signals;

a set of first state machines, the first state machines being used to select one state among a plurality of possible states for each main artificial proprioceptor with the corresponding data and derivative signals;

means for generating the phase of locomotion portion using the states of the main artificial proprioceptors; and a second state machine, the second state means being used to select the portion of locomotion among a plurality of possible portions of locomotion using events associated to the data signals.

In accordance with a further aspect of the present invention, there is provided a control system for controlling an actuated prosthesis in real time, the system comprising:

a plurality of main artificial proprioceptors;

means for obtaining a first and a second derivative signal for each data signal;

means for obtaining a third derivative signal for at least one of the data signals;

a set of first state machines, the first state machines being used to select one state among a plurality of possible states for each main artificial proprioceptor with the corresponding data and derivative signals;

means for generating the phase of locomotion portion using the states of the main artificial proprioceptors;

a second state machine, the second state machine being used to select the portion of locomotion among a plurality of possible portions of locomotion using events associated to data signals;

means for calculating a locomotion speed value;

means for storing a lookup table comprising coefficient values with reference to at least phases of locomotion, portions of locomotion and locomotion speed values;

means for determining actual coefficient values from the lookup table using at least the phase of locomotion portion, the portion of locomotion and the locomotion speed value;

means for calculating at least one dynamic parameter value of the actuated prosthesis using the coefficient values from the lookup table; and means for converting the dynamic parameter value into an output signal to control the actuated prosthesis.

These and other aspects of the present invention are described in or apparent from the following detailed description, which description is made in conjunction with the accompanying figures.

ACRONYMS

Figure 1:
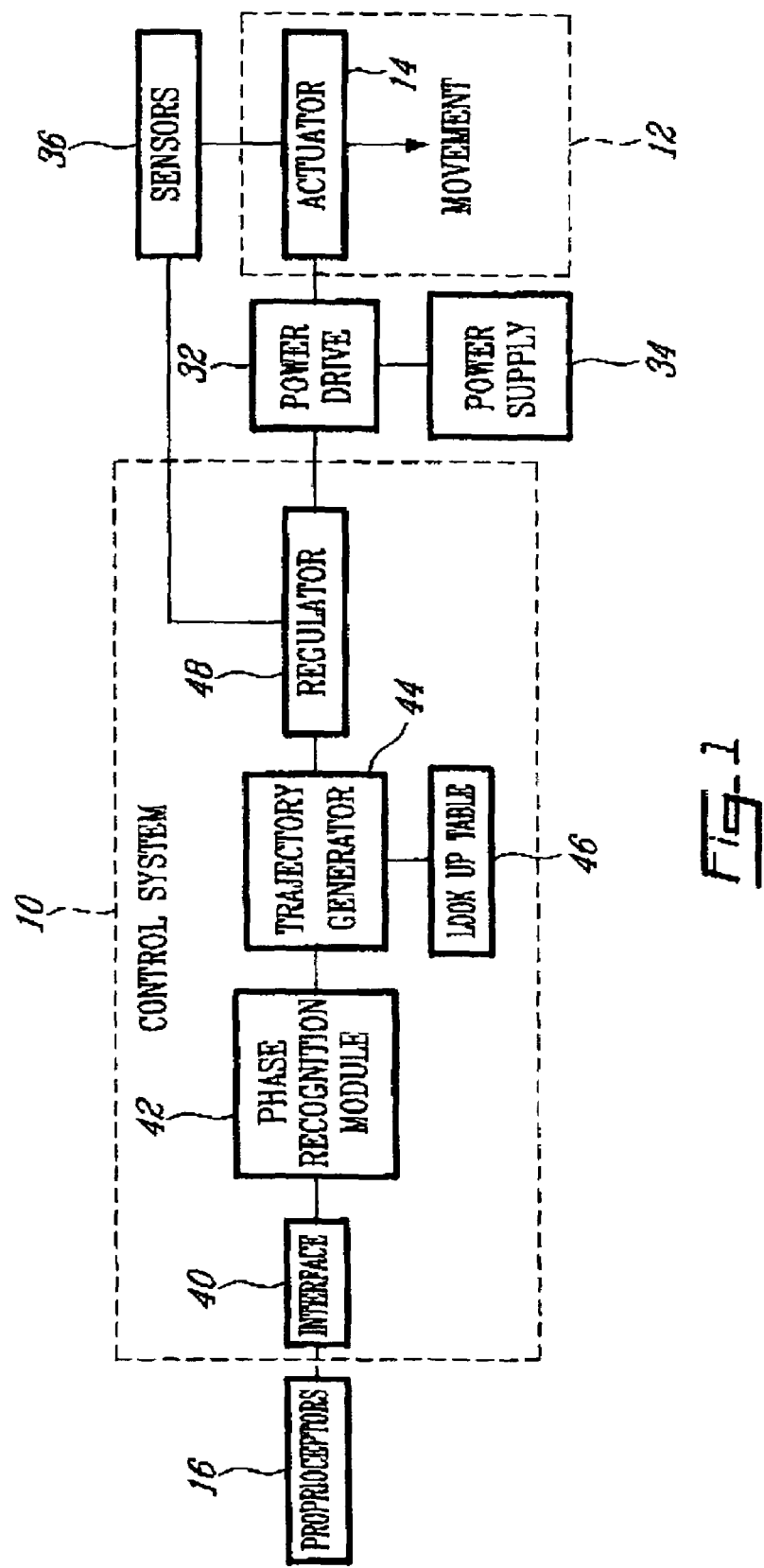
FIG. 1 is a block diagram showing the control system in accordance with a preferred embodiment of the present invention.

The detailed description and figures refer to the following technical acronyms:

A/D Analog/Digital

BDW "Downward Inclined Walking—Beginning path" portion of locomotion

BGD "Going Down Stairs—Beginning path" portion of locomotion

BGU "Going Up Stairs—Beginning path portion of locomotion

BTW "Linear Walking—Beginning path" portion of locomotion

BTW_SWING Detection of typical walking $g_{r\_leg}$ during leg swing

BUW "Upward Inclined Walking—Beginning path" portion of locomotion

CDW "Downward Inclined Walking—Cyclical path" portion of locomotion

CGD "Going Down Stairs—Cyclical path" portion of locomotion

CGU "Going Up Stairs—Cyclical path" portion of locomotion

CTW "Linear Walking—Cyclical path" portion of locomotion

CUW "Upward Inclined Walking—Cyclical path" portion of locomotion

ECW "Curve Walking Path" portion of locomotion

EDW "Downward Inclined Walking—Ending path" portion of locomotion

EGD "Going Down Stairs—Ending path" portion of locomotion

EGU "Going Up Stairs—Ending path" portion of locomotion

ETW "Linear Walking—Ending path" portion of locomotion

EUW "Upward Inclined Walking—Ending path" portion of locomotion

FR_BIN$_x$ Detection of a positive $f_{rx}$

FRfst_BIN$_x$ Detection of positive first differentiation of $f_{rx}$

FRsec_BIN$_x$ Detection of positive second differentiation of $f_{rx}$

FRtrd_BIN$_x$ Detection of positive third differentiation of $f_{rx}$

FR_HIGH$_x$ Detection of $f_{rx}$ level above the STA envelope

FR_LOW$_x$ Detection of $f_{rx}$ level between the zero envelope and the STA envelope FSR Force Sensing Resistor GR_POS$_y$ Detection of a positive $g_{ry}$ MIN_SIT Detection of a minimum time in portion SIT MP Metatarsophalangeal PID Proportional-Integral-Differential PKA_SDWSit down knee angle PKA_ETWEnd walking knee angle PKA_STA Stance knee angle PKA_SIT Sit down knee angle PKA_SUP_RAMPStanding up knee angle PPMV Plantar Pressure Maximal Variation PPS Plantar Pressure Sensor PRM Phase Recognition Module REG Regulator RF Radio Frequency SDW "Sitting down" portion of locomotion SIT "Sitting" portion of locomotion STA "Stance of feet" portion of locomotion STA_BIN Detection of a static evolution of all $f_{rx}$ STATIC_GR$_y$ Detection of $g_{ry}$ level below the zero angular speed envelope and the zero acceleration envelope sum$_a$ Localized plantar pressure signal of left foot sum$_b$ Localized plantar pressure signal of right foot sum$_c$ Localized plantar pressure signal of both calcaneus sum$_d$ Localized plantar pressure signal of both MP sum$_e$ Localized plantar pressure signal of both feet SUM_BIN$_y$ Non-Zero of sum$_y$ SUP "Standing Up" portion of locomotion SVD Singular Values Decomposition SWING$_y$ Detection of a swing prior to a foot strike TG Trajectory Generator XHLSB Heel Loading State Bottom (X=Left (L) or Right (R))

XHLSM Heel Loading State Middle (X=Left (L) or Right (R))

XHLST Heel Loading State Top (X=Left (L) or Right (R))

XHSTA Heel STAtic state (X=Left (L) or Right (R))

XHUSB Heel Unloading State Bottom (X=Left (L) or Right (R))

XHUST Heel Unloading State Top (X=Left (L) or Right (R))

XHZVS Heel Zero Value State (X=Left (L) or Right (R))

XMLSM MP Loading State Middle (X=Left (L) or Right (R))

XMLST MP Loading State Top (X=Left (L) or Right (R))

XMSTA MP STAtic state (X=Left (L) or Right (R))

XMUSB MP Unloading State Bottom (X=Left (L) or Right (R))

XMUST MP Unloading State Top (X=Left (L) or Right (R))

XMZVS MP Zero Value State (X=Left (L) or Right (R))

ZV_FRfst$_x$ Threshold to consider the first differentiation of $f_{rx}$ to be positive.

ZV_FRsec$_x$ Threshold to consider the second differentiation of $f_{rx}$ to be positive.

ZV_FRtrd$_x$ Threshold to consider the third differentiation of $f_{rx}$ to be positive.

ZV_FR$_x$ Threshold to consider $f_{rx}$ to be positive

ZV_SUMfst Threshold to consider the absolute value of the $1^{st}$ diff. of sum$_y$ to be positive.

ZV_SUMsec Threshold to consider the absolute value of the $2^{nd}$ diff. of sum$_y$ to be positive

DETAILED DESCRIPTION OF THE INVENTION

The appended figures show a control system (10) in accordance with the preferred embodiment of the present invention. It should be understood that the present invention is not limited to the illustrated implementation since various changes and modifications may be effected herein without departing from the scope of the appended claims.

FIG. 1 shows the control system (10) being combined with an autonomous actuated prosthesis for amputees. It is particularly well adapted for use with an actuated leg prosthesis for above-knee amputees, such as the prostheses (12) shown in FIGS. 2 and 3. Unlike conventional prostheses, these autonomous actuated prostheses (12) are designed to supply the mechanical energy necessary to move them by themselves. The purpose of the control system (10) is to provide the required signals allowing to control an actuator (14). To do so, the control system (10) is interfaced with the amputee using artificial proprioceptors (16) to ensure proper coordination between the amputee and the movements of the actuated prosthesis (12). The set of artificial proprioceptors (16) captures information, in real time, about the dynamics of the amputee's movement and provides that information to the control system (10). The control system (10) is then used to determine the joint trajectories and the required force or torque that must be applied by the actuator (14) in order to provide coordinated movements.

Figure 2:
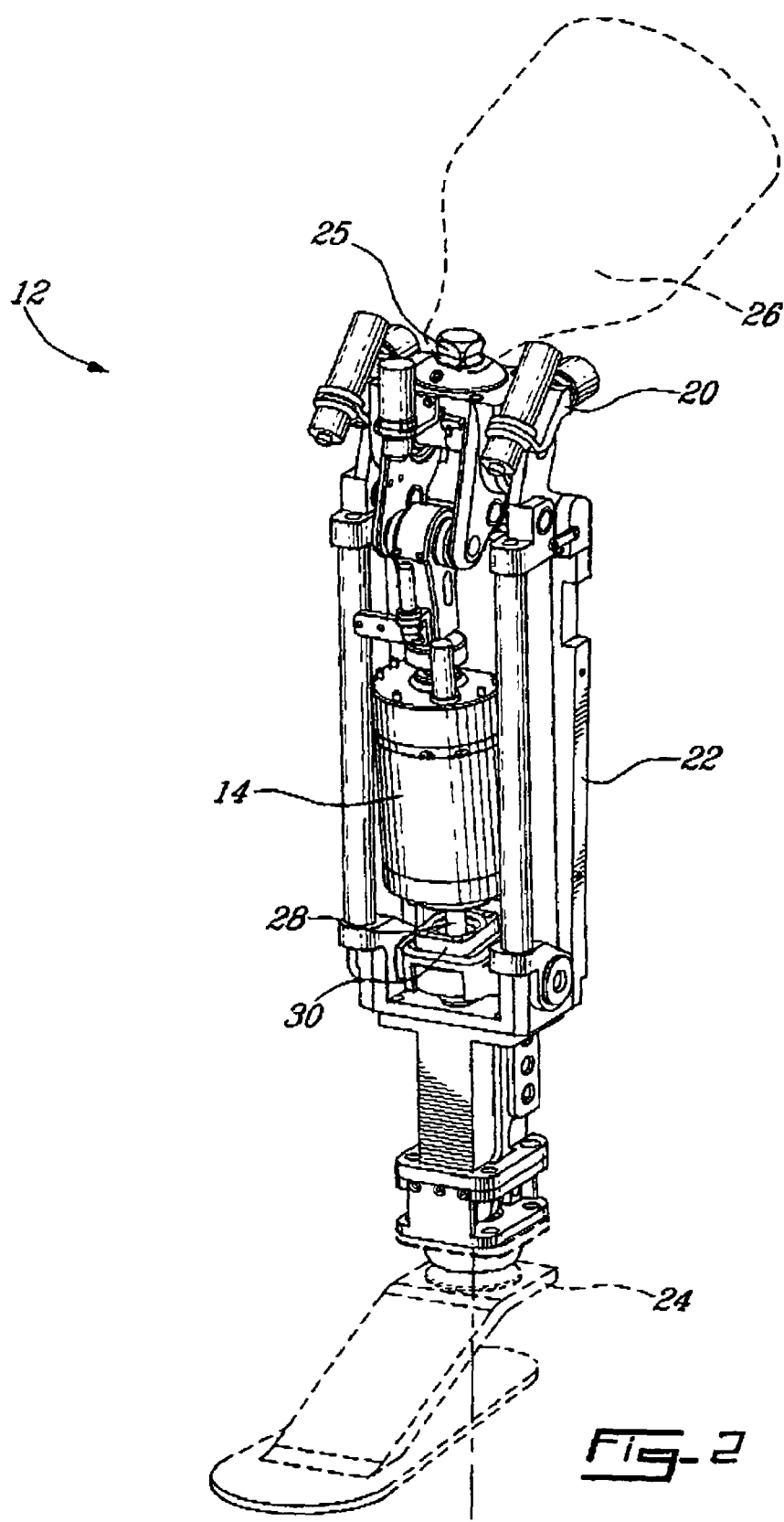
FIG. 2 is a perspective view of an example of an actuated prosthesis with a front actuator configuration.

FIG. 2 shows an example of an actuated leg prosthesis (12) for an above-knee amputee. This prosthesis (12) is powered by a linear actuator (14). The actuator (14) moves a knee member (20) with reference to a trans-tibial member (22), both of which are pivotally connected using a first pivot axis. More sophisticated models may be equipped with a more complex pivot or more than one pivot at that level.

An artificial foot (24) is provided under a bottom end of the trans-tibial member (22). The knee member (20) comprises a connector (25) to which a socket (26) can be attached. The socket (26) is used to hold the sump of the amputee. The design of the knee member (20) is such that the actuator (14) has an upper end connected to another pivot on the knee member (20). The bottom end of the actuator (14) is then connected to a third pivot at the bottom end of the trans-tibial member (22). In use, the actuator (14) is operated by activating an electrical motor therein. This rotates, in one direction or another, a screw (28). The screw (28) is then moved in or out with reference to a follower (30), thereby changing the relative angular position between the two movable parts, namely the knee member (20) and the trans-tibial member (22).

Figure 3:
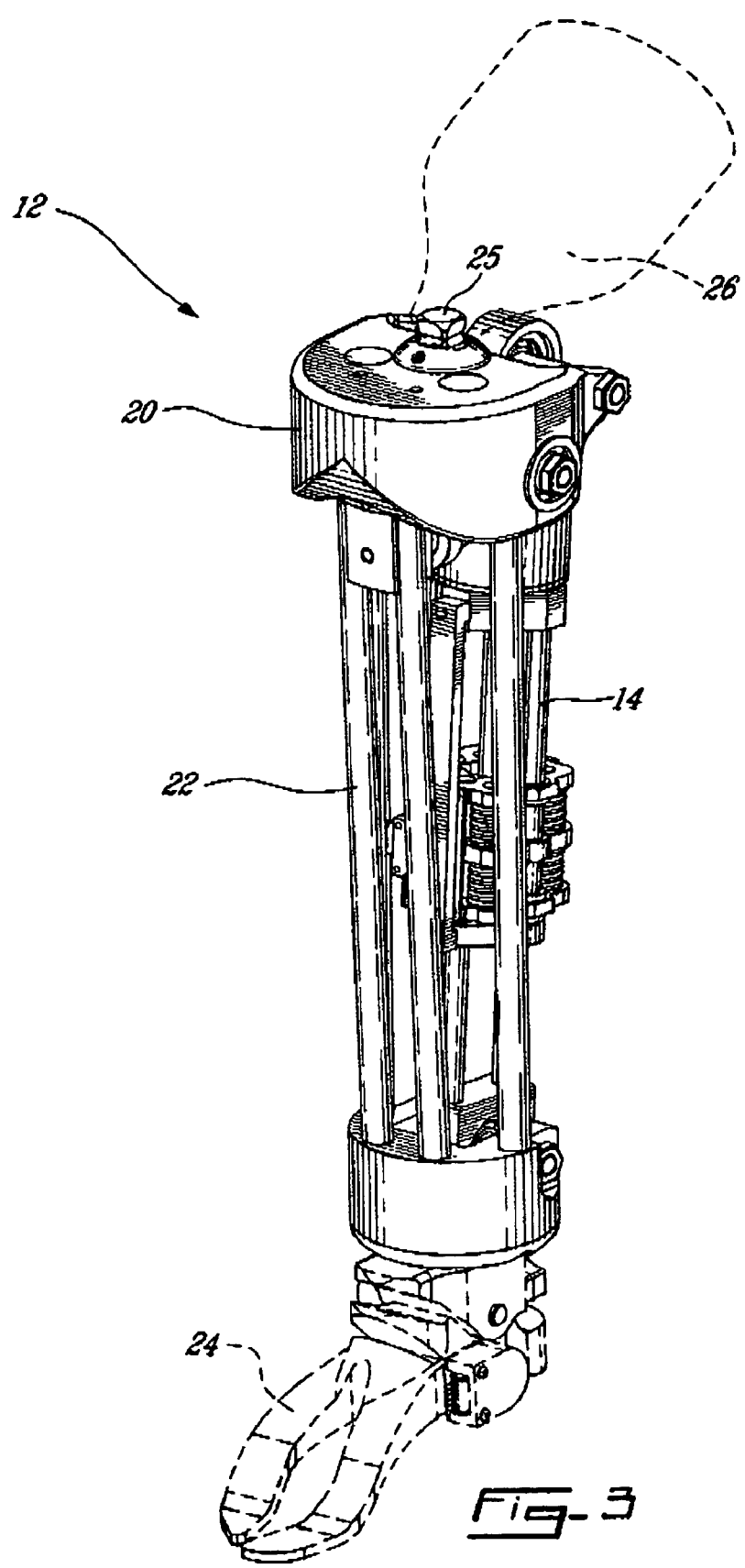
FIG. 3 is a perspective view of an example of an actuated prosthesis with a rear actuator configuration.

FIG. 3 shows an actuated leg prosthesis (12) in accordance to a rear actuator configuration. This embodiment is essentially similar to that of FIG. 2 and is illustrated with a different model of actuator (14).

It should be noted that the present invention is not limited to the mechanical configurations illustrated in FIGS. 2 and 3. The control system (10) may be used with a leg prosthesis having more than one joint. For instance, it can be used with a prosthesis having an ankle joint, a metatarsophalangeal joint or a hip joint in addition to a knee joint. Moreover, instead of a conventional socket, osseo-integrated devices could also be used, ensuring a direct attachment between the mechanical component of the prosthesis and the amputee skeleton. Other kinds of prostheses may be used as well.

Referring back to FIG. 1, the information provided by the artificial proprioceptors (16) are used by the control system (10) to generate an output signal. These output signals are preferably sent to the actuator (14) via a power drive (32) which is itself connected to a power supply (34), for instance a battery, in order to create the movement. The power drive (32) is used to control the amount of power being provided to the actuator (14). Since the actuator (14) usually includes an electrical motor, the power drive (32) generally supplies electrical power to the actuator (14) to create the movement.

Preferably, feedback signals are received from sensors (36) provided on the prosthesis (12). In the case of an actuated leg prosthesis (12) such as the one illustrated in FIGS. 2 and 3, these feedback signals may indicate the relative position measured between two movable parts and the torque between them. This option allows the control system (10) to adequately adjust the output signal. Other types of physical parameters may be monitored as well.

The control system (10) shown in FIG. 1 comprises an interface (40) through which data signals coming from the artificial proprioceptors (16) are received. They may be received either from an appropriate wiring or from a wireless transmission. In the case of actuated leg prostheses for above-knee amputees, data signals from the artificial proprioceptors (16) provided on a healthy leg are advantageously sent through the wireless transmission using an appropriate RF module. For example, a simple off-the-shelf RF module with a dedicated specific frequency, such as 916 MHz, may be used. For a more robust implementation though, the use of a RF module with a spread spectrum or frequency hopper is preferable. Of course, other configurations may be used as well, such as a separate A/D converter, different resolution or sampling values and various combinations of communication link technologies such as wired, wireless, optical, etc.

The control system (10) further comprises a part called "Phase Recognition Module" or PRM (42). The PRM (42) is a very important part of the control system (10) since it is used to determine two important parameters, namely the portion of locomotion and the phase of locomotion portion. These parameters are explained later in the text. The PRM (42) is connected to a Trajectory Generator, or TG (44), from which dynamic parameters required to control the actuated prosthesis (12) are calculated to create the output signal. A lookup table (6) is stored in a memory connected to the TG (44). Moreover, the control system (10) comprises a regulator (48) at which the feedback signals are received and the output signal can be adjusted.

Software residing on an electronic circuit board contains all the above mentioned algorithms enabling the control system (10) to provide the required signals allowing to control the actuator (14). More specifically, the software contains the following three modules: the Phase Recognition Module (PRM), the Trajectories Generator (TG) and the Regulator (REG). Of course, any number of auxiliary modules may be added.

The artificial proprioceptors (16) preferably comprise main artificial proprioceptors and auxiliary artificial proprioceptors. The main artificial proprioceptors are preferably localized plantar pressure sensors which measure the vertical plantar pressure of a specific underfoot area, while the auxiliary artificial proprioceptors are preferably a pair of gyroscopes which measure the angular speed of body segments of the lower extremities and a kinematic sensor which measures the angle of the prosthesis knee joint. The plantar pressure sensors are used under both feet, including the artificial foot. It could also be used under two artificial feet if required. One of the gyroscopes is located at the shank of the normal leg while the other is located on the upper portion of the prosthesis above the knee joint. As for the kinematic sensor, it is located at the prosthesis knee joint. Other examples of artificial proprioceptors (16) are neuro-sensors which measure the action potential of motor nerves, myo-electrical electrodes which measure the internal or the external myoelectrical activity of muscles, needle matrix implants which measure the cerebral activity of specific region of the cerebrum cortex such as motor cortex or any other region indirectly related to the somatic mobility of limbs or any internal or external kinematic and/or kinetic sensors which measure the position and the torque at any joints of the actuated prosthesis. Of course, depending on the application, additional types of sensors which provide information about various dynamics of human movement may be used.

Figure 4:
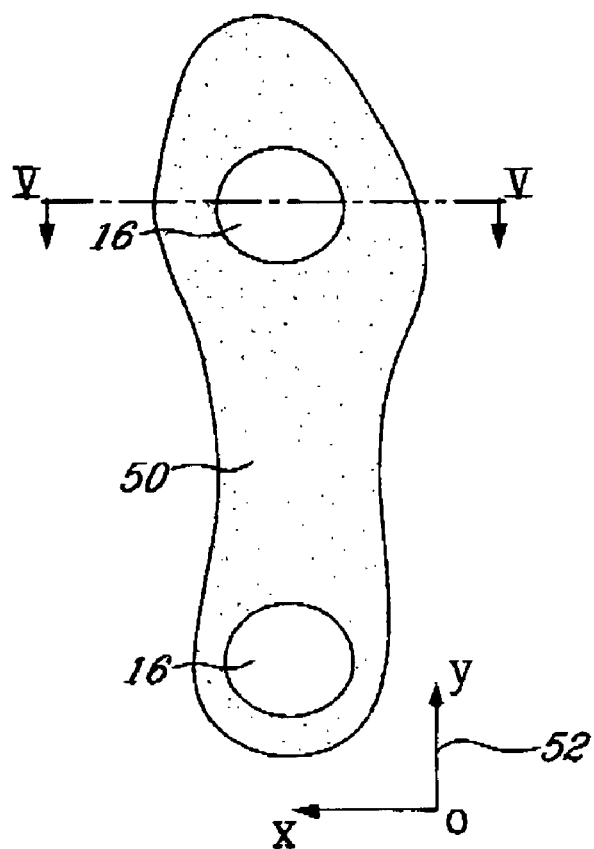
FIG. 4 is an upper schematic view of an insole provided with plantar pressure sensors.

FIG. 4 shows a right insole (10) provided with two plantar pressure sensors (16) positioned at strategic locations. Their size and position were defined in accordance with the stability and the richness (intensity) of the localized plantar pressure signals provided by certain underfoot areas during locomotion. Experimentation provided numerous data concerning the spatial distribution of foot pressures and more specifically on the Plantar Pressure Maximal Variation (PPMV) during locomotion. The PPMV, denoted $\Delta_{max} f_{r,ij}$, was defined as the maximum variation of the plantar pressure at a particular point (underfoot area of coordinate i,j) during locomotion. The X-Y axis (52) in FIG. 4 was used to determine the i,j coordinates of each underfoot area.

A PPMV of a given underfoot area of coordinates i,j during a given step denoted event x, is defined as stable, through a set of N walking steps, if the ratio of the absolute difference between this PPMV and the average PPMV over the set is inferior to a certain value representing the criteria of stability, thus:

$$\left( \frac{\left| \Delta_{max} f_{r,U} \right|_x - \frac{\sum_{n=0}^{N} \Delta_{max} f_{r,U} \big|_n}{N}}{\frac{\sum_{n=0}^{N} \Delta_{max} f_{r,U} \big|_n}{N}} \right) \cdot 100\% \leq (S\%) \quad \text{Equation 1}$$

where $\Delta_{max} f_{r,ij}\big|_x$ is the PPMV localized at underfoot area of coordinates i, j during the event x, thus $\Delta_{max} f_{r,ij}\big|_x = f_{r,ij}{}^{max}(k)\big|_{k \to 0 \ to \ K} - f_{r,ij}{}^{min}(k)\big|_{k \to 0 \ to \ K}$ for the event x K is the number of samples (frames),
N is the number of steps in the set,
S is the chosen criteria to define if a given PPMV is stable.

A PPMV of a given underfoot area of coordinates i,j during a given step denoted event x, is defined as rich in information, through a set of N walking steps, if the ratio between the PPMV and the average PPMV of the set is superior to certain value representing the criteria of richness. thus:

$$\Delta_{max} f_{r,U}\big|_x \geq (R\%) \cdot \left( \frac{\sum_{n=0}^{N} \Delta_{max} f_{r,U}\big|_n}{N} \right)\bigg|_{max}{}^{i,j} \quad \text{Equation 2}$$

where $\Delta_{max} f_{r,ij}\big|_x$ is the PPMV localized at underfoot area of coordinates i, j during the event x, thus $\Delta_{max} f_{r,ij}\big|_x = f_{r,ij}{}^{max}(k)\big|_{k \to 0 \ to \ K} - f_{r,ij}{}^{min}(k)\big|_{k \to 0 \ to \ K}$ for the event x K is the number of samples (frames),
N is the number of steps in the set,
R is the chosen criteria to define if a given PPMV is rich in information.

It was found by experimentation that the size and the position of plantar pressure sensor are well defined when the criteria are set at 5% and 10% for the stability and the richness PPMV respectively. As a result, it was found that the calcaneus and the Metatarsophalangeal (MP) regions are two regions of the foot sole where the PPMV may be considered as providing a signal that is both stable and rich in information.

Figure 5:
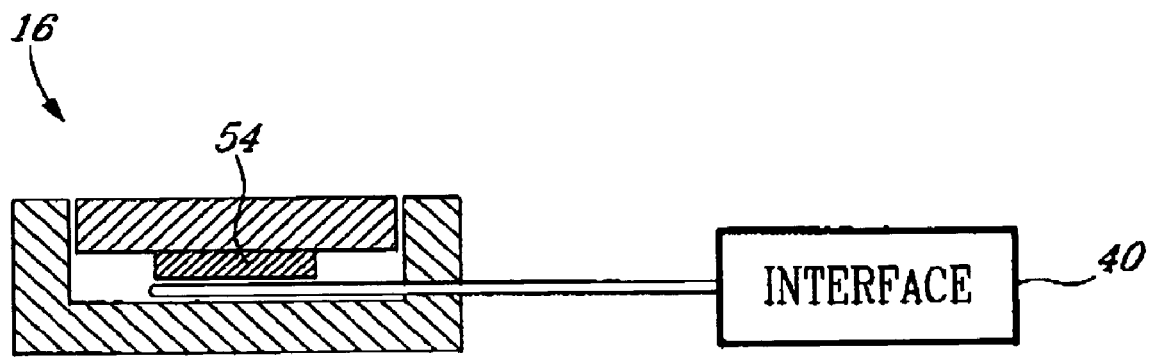
FIG. 5 is a cross sectional view of a sensor shown in FIG. 4.

In FIG. 4, the plantar pressure sensors (16) are provided in a custom-made insole (10), preferably in the form of a standard orthopedic insole, that is modified to embed the two sensors (16) for the measurement of two localized plantar pressures. Each sensor (16), as shown in FIG. 5, is preferably composed of a thin Force-Sensing Resistor (FSR) polymer cell (54) directly connected to the interface (40) or indirectly using an intermediary system (not shown), for instance a wireless emitter. Mechanical adapters may be used if FSR cells of appropriate size are not available. The FSR cell (54) has a decreasing electrical resistance in response to an increasing force applied perpendicularly to the surface thereof. Each cell (54) outputs a time variable electrical signal for which the intensity is proportional to the total vertical plantar pressure over its surface area.

The normalized position of the pressure sensors and their size are shown in Table 1, where the length L and the width W are respectively the length and the width of the subject's foot. The coefficients in Table 1 have been obtained by experimentation. A typical diameter for the plantar pressure sensors (16) is between 20 and 30 mm.

TABLE 1

Normalized position and size of pressure sensors

| Area | Position (X, Y) | Size (diameter) |
| --- | --- | --- |
| Calcaneus | (0.51 · W, 0.14 · L) | 0.29 · $\sqrt{L \cdot W}$ |
| MP | (0.47 · W, 0.76 · L) | 0.24 · $\sqrt{L \cdot W}$ |

In use, the PRM (42) ensures, in real-time, the recognition of the phase of locomotion portion and the portion of locomotion of an individual based on the information provided by the artificial proprioceptors (16). The PRM (42) is said to operate in real time, which means that the computations and other steps are performed continuously and with almost no delay.

In accordance with the present invention, it was found that data signals received from individual artificial proprioceptors (16) can provide enough information in order to control the actuator (14) of an actuated prosthesis (12). For instance, in the case of plantar pressure sensors, it has been noticed experimentally that the slope (first derivative), the sign of the concavity (second derivative) and the slope of concavity (third derivative) of the data signals received from plantar pressure sensors, and of combinations of those signals, give highly accurate and stable information on the human locomotion. The PRM (42) is then used to decompose of the human locomotion into three levels, namely the states of each artificial proprioceptor (16), the phase of locomotion portion and the portion of locomotion. This breakdown ensures the proper identification of the complete mobility dynamics of the lower extremities in order to model the human locomotion.

The actual states of each main artificial proprioceptor depict the first level of the locomotion breakdown. This level is defined as the evolution of the main artificial proprioceptors' sensors during the mobility of the lower extremities. Each sensor has its respective state identified from the combination of its data signal and its first three differential signals. For the main artificial proprioceptors of the preferred embodiment, which provide information about localized plantar pressures, it has been discovered experimentally that the localized plantar pressures signals located at the calcaneous and at the metatarsophalangeal (MP) regions may be grouped into seven and six states respectively.

For the sensors at the calcaneous regions, the states are preferably as follows:

XHLSB Heel Loading State Bottom (X=Left (L) or Right (R))

XHLSM Heel Loading State Middle (X=Left (L) or Right (R))

XHLST Heel Loading State Top (X=Left (L) or Right (R))

XHSTA Heel STAtic State (X=Left (L) or Right (R))

XHUSB Heel Unloading State Bottom (X=Left (L) or Right (R))

XHUST Heel Unloading State Top (X=Left (L) or Right (R))

XHZVS Heel Zero Value State (X=Left (L) or Right (R))

For the sensors at the MP regions, the states are preferably as follows:

XMLSB MP Loading State Bottom (X=Left (L) or Right (R))

XMLST MP Loading State Top (X=Left (L) or Right (R))
XMSTA MP STAtic State (X=Left (L) or Right (R))
XMUSB MP Unloading State Bottom (X=Left (L) or Right (R))
XMUST MP Unloading State Top (X=Left (L) or Right (R))
XMZVS MP Zero Value State (X=Left (L) or Right (R))

Identifying the states at each sensor allows to obtain the second level of the locomotion breakdown, referred to as the phase of locomotion portion. The phase of locomotion portion is defined as the progression of the subject's mobility within the third level of locomotion breakdown, namely the portion of locomotion. This third level of the locomotion breakdown defines the type of mobility the subject is currently in, such as, for example, standing, sitting or climbing up stairs. Each locomotion portion contains a set of sequential phases illustrating the progression of the subject's mobility within that locomotion portion. The phase sequence mapping for each locomotion portion has been identified by experimentation according to the evolution of the state of the localized plantar pressures throughout the portion.

The portions of locomotion are preferably as follows:
BDW "Downward Inclined Walking—Beginning path"
BGD "Going Down Stairs—Beginning path"
BGU "Going Up Stairs—Beginning path
BTW "Linear Walking—Beginning path"
BUW "Upward Inclined Walking—Beginning path"
CDW "Downward Inclined Walking—Cyclical path"
CGD "Going Down Stairs—Cyclical path"
CGU "Going Up Stairs—Cyclical path"
CTW "Linear Walking—Cyclical path"
CUW "Upward Inclined Walking—Cyclical path"
ECW "Curve Walking Path"
EDW "Downward Inclined Walking—Ending path"
EGD "Going Down Stairs—Ending path"
EGU "Going Up Stairs—Ending path"
ETW "Linear Walking—Ending path"
EUW "Upward Inclined Walking—Ending path"
SDW "Sitting down"
SIT "Sitting"
STA "Stance of feet"
SUP "Standing Up"

Figure 6:
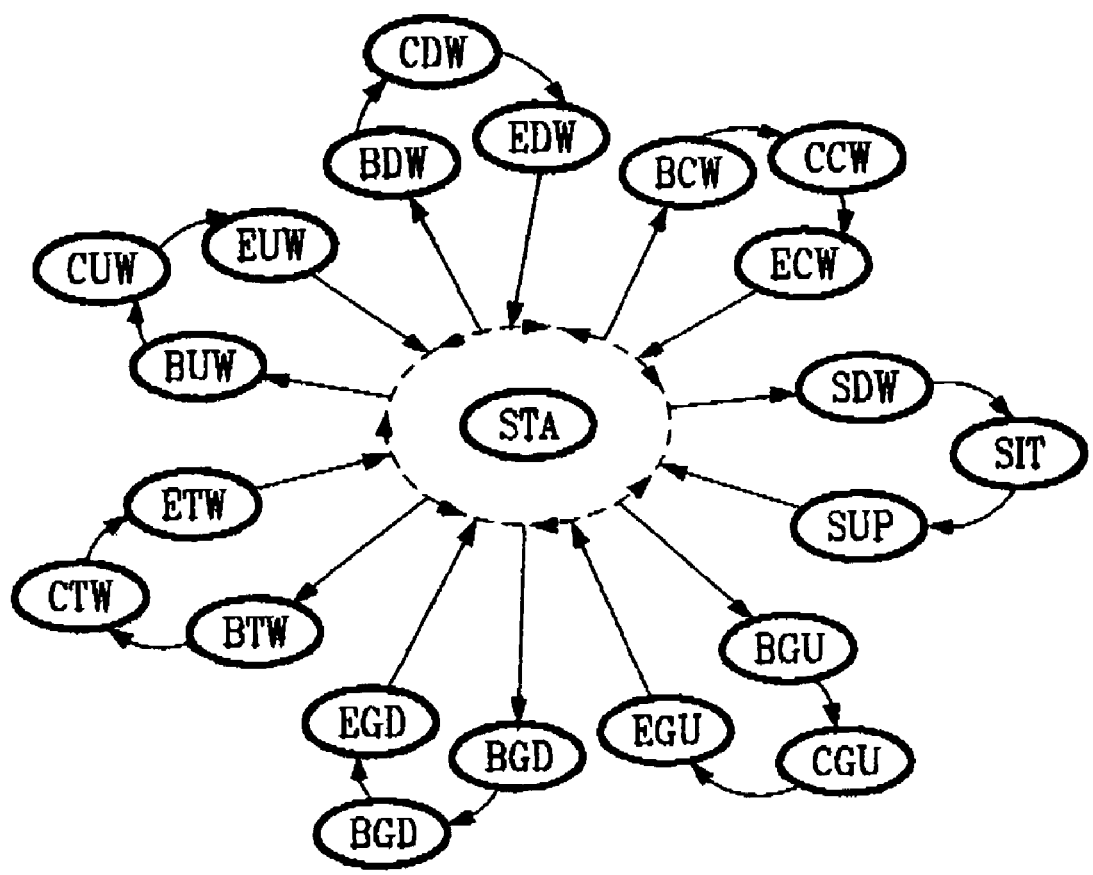
FIG. 6 is an example of a state machine diagram for the selection of the portion of locomotion.

FIG. 6 illustrates an example of the state machine concerning these various portions of locomotion.

Figure 7:
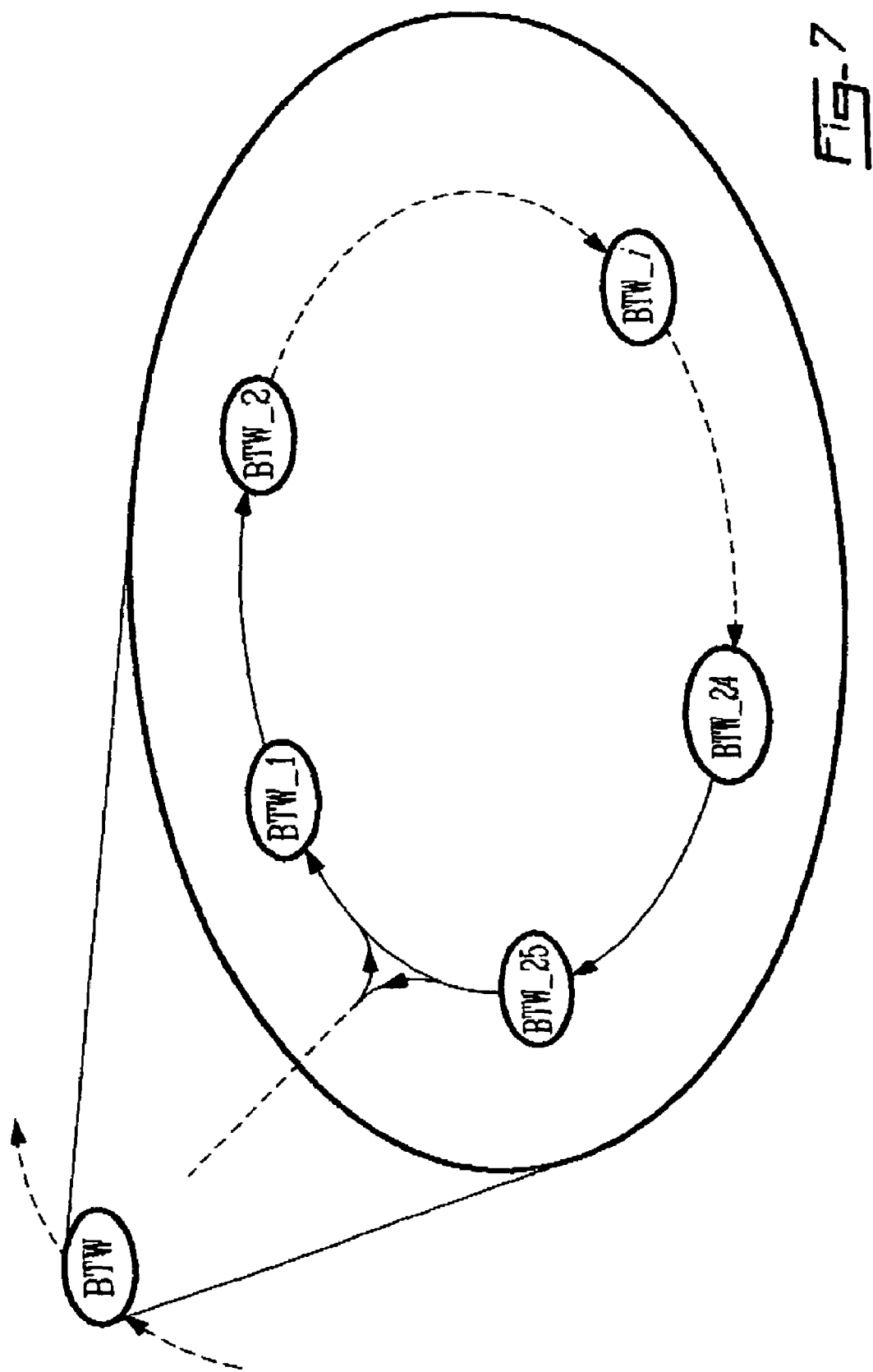
FIG. 7 is an example of the phases of locomotion portion within one portion of locomotion (BTW) in the state machine diagram shown in FIG. 6.

FIG. 7 shows an example of a phase sequence mapping, BTW_1 to BTW_25, for the Beginning Path of Linear Walking (BTW) portion of locomotion. All locomotion portions have similar patterns of phase sequence mapping, though the number of phases may vary from one locomotion portion to another. The number of phases depends on the desired granularity of the decomposition of the locomotion portion. The phases are determined experimentally by observing the states of the four localized plantar pressures at specific time intervals, which are determined by the desired granularity. Since a phase is the combination of the states of the four localized plantar pressures, the phase boundary conditions are therefore defined as the combination of each localized plantar pressure state boundary conditions.

For the selection of the portion of locomotion the subject is in, the algorithm uses the state machine approach. For this purpose, the algorithm uses a set of events which values define the conditions, or portion boundary conditions, to pass from one locomotion portion to another. These events are identified by experimentation according to the evolution of the localized plantar pressure signals, the complementary signals and their first three differentials, as well as the signals from the auxiliary artificial proprioceptors, when the subject passes from one locomotion portion to another.

Having determined the states of the main artificial proprioceptors' sensors, the phase of locomotion portion and portion of locomotion of the subject, the TG (44) can be used to calculate one or more dynamic parameter values to be converted to an output signal for the control of the actuator. Examples of dynamic parameter values are the angular displacement and the torque (or moment of force) at the knee joint of the actuated leg prosthesis (12). Since these values are given in real time, they provide what is commonly referred to as the "system's trajectory". At any time k during the subject's locomotion, a mathematical relationship is selected according to the state of the whole system, that is the states of the main artificial proprioceptors, the phase of locomotion portion, the portion of locomotion and the walking speed. Following which, the angular displacement $\theta_{kn}$ and the moment of force $m_{kn}$ are then computed using simple time dependant equations and static characteristics associated with the state of the system, thereby providing the joint's trajectory to the knee joint member. This process is repeated throughout the subject's locomotion.

Figure 8A:
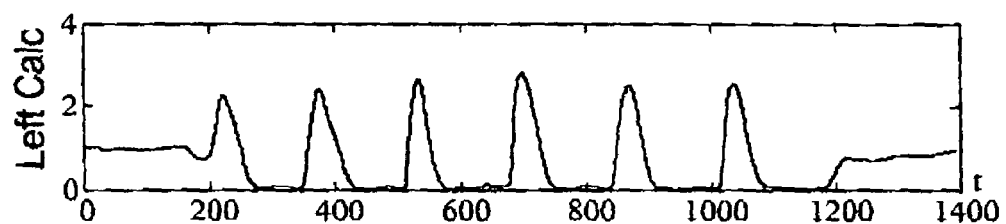
FIGS. 8a to 8d are examples of four data signals using plantar pressure sensors during typical walking on flat ground.
Figure 8B:
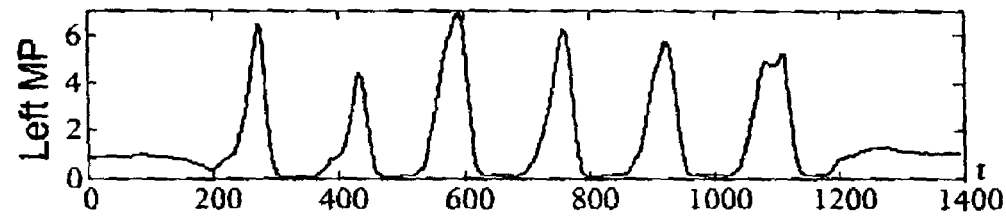
Figure 8C:
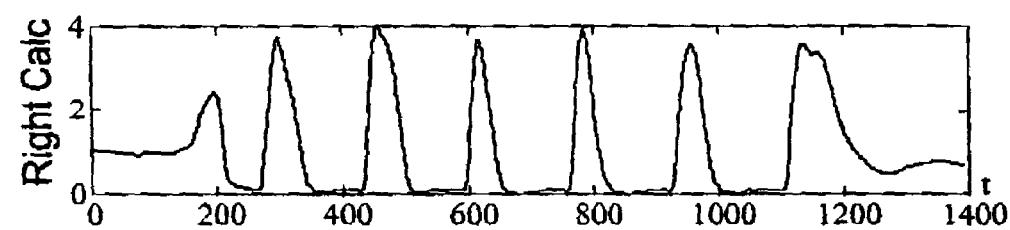
Figure 8D:
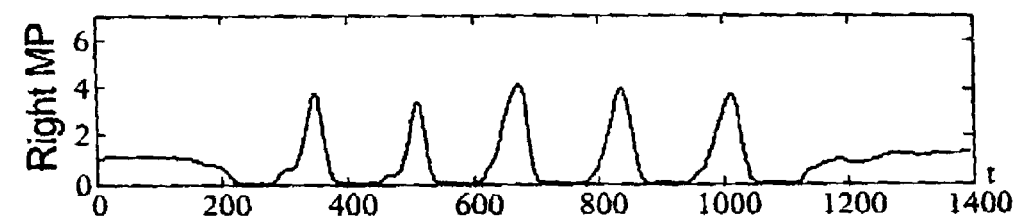
Figure 9A:
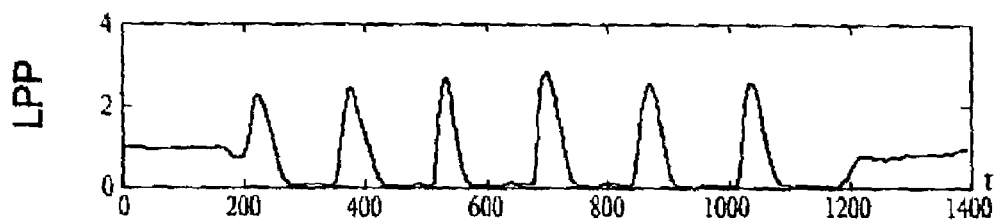
FIGS. 9a to 9d give an example of a data signal obtained from a plantar pressure sensor at the calcaneus region and its first three differentials.
Figure 9B:
Figure 9C:
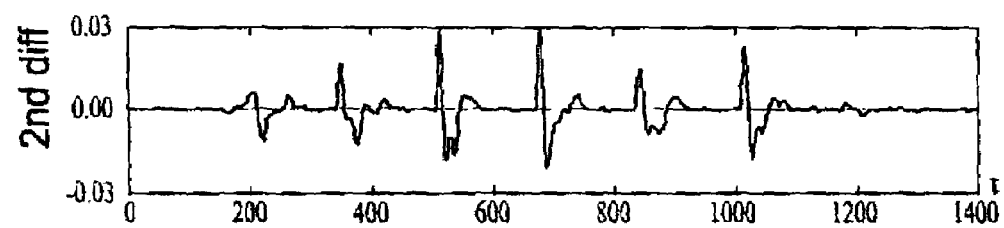
Figure 9D:
Figure 10A:
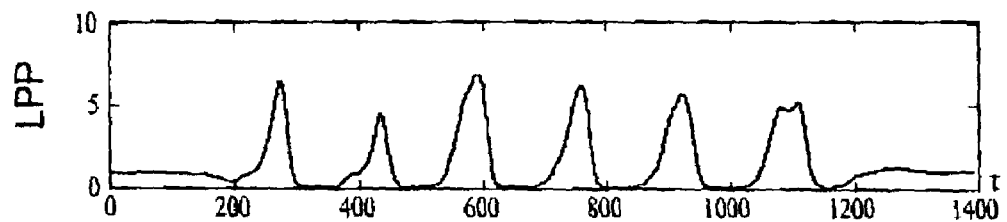
FIGS. 10a to 10d give an example of a data signal obtained from a plantar pressure sensor at the metatarsophalangeal (MP) region and its first three differentials.
Figure 10B:
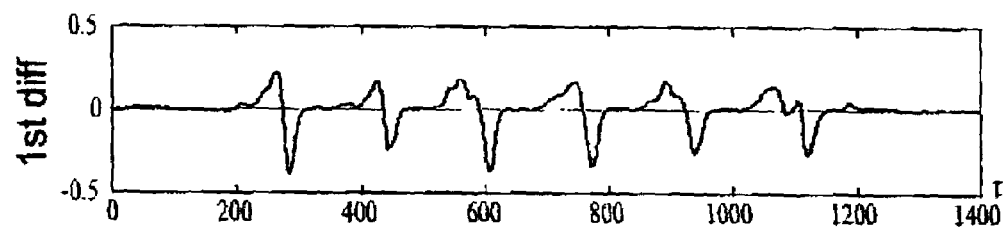
Figure 10C:
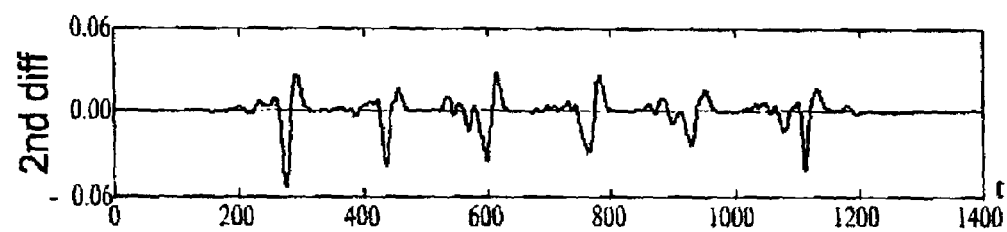
Figure 10D:
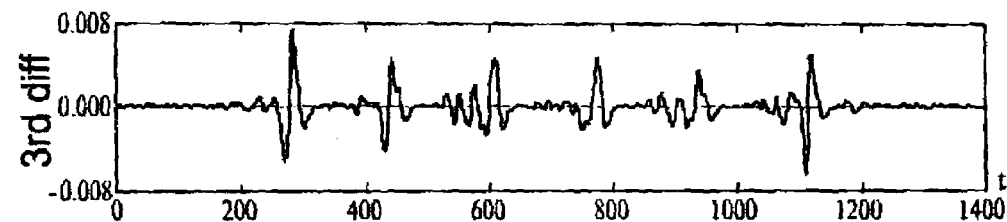
Figure 11A:
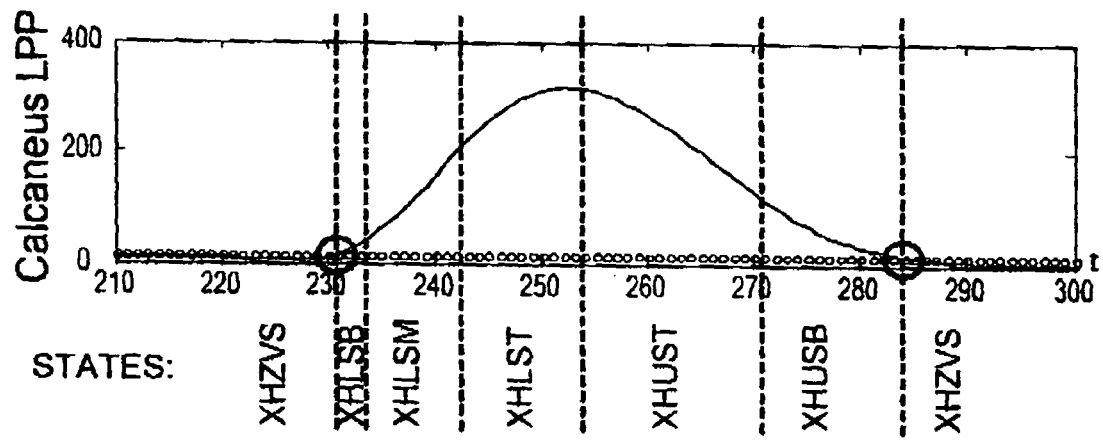
FIGS. 11a to 11d give an example of the states of a plantar pressure sensor with reference to the data signal and its three first differentiations for a plantar pressure sensor at the calcaneous region.
Figure 11B:
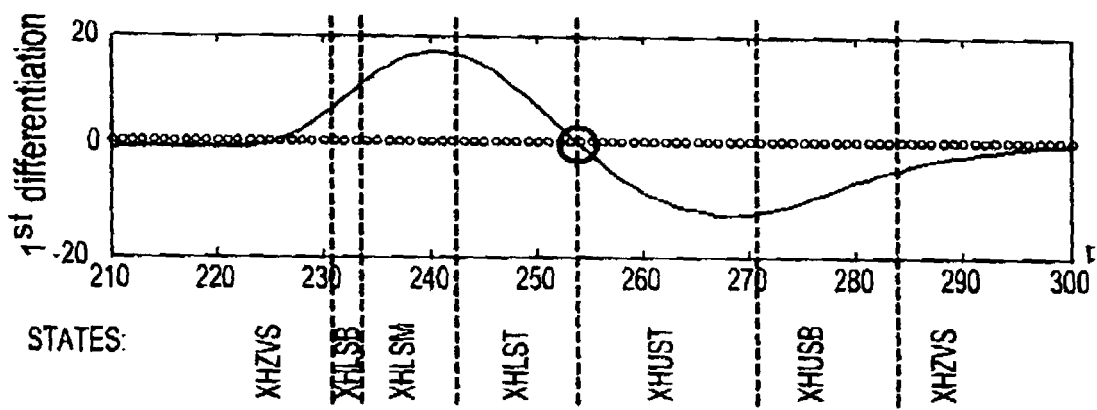
Figure 11C:
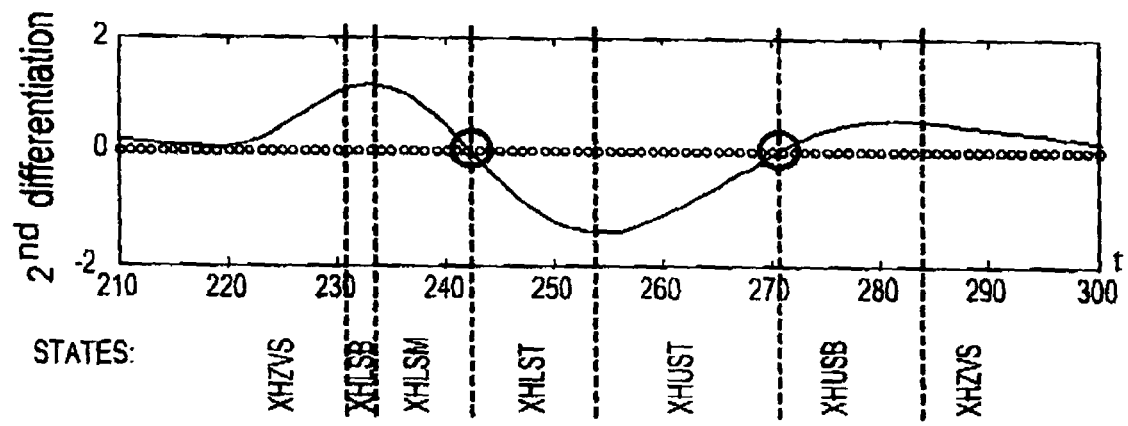
Figure 11D:
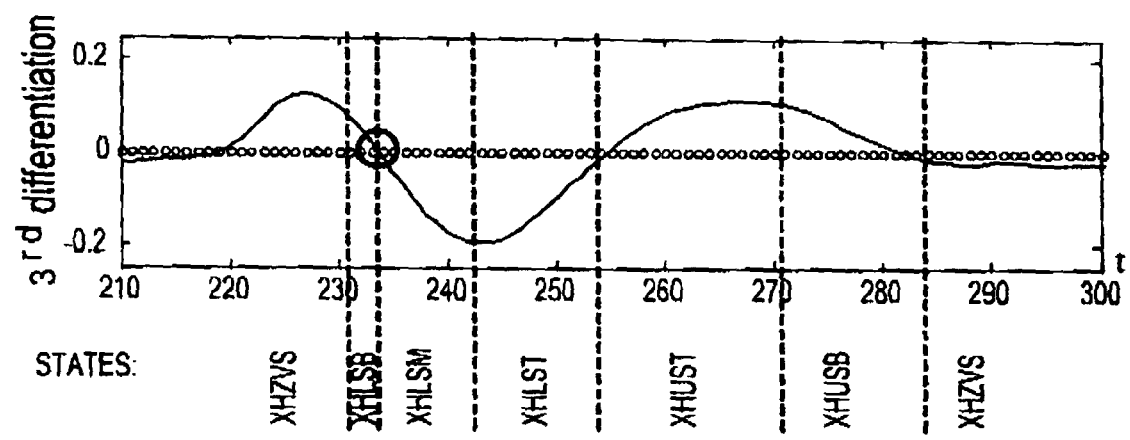

FIGS. 8a to 8d show examples of data signals from the four localized plantar pressure sensors (16) during a standard walking path at 109,5 steps/minute. The four signals, $f_{r1}(t)$, $f_{r2}(t)$, $f_{r3}(t)$ and $f_{r4}(t)$, correspond to the variation in time of the localized plantar pressure at the calcaneus region of the left foot (FIG. 8a), the MP region of the left foot (FIG. 8b), the calcaneus region of the right foot (FIG. 8c), and the MP region of the right foot (FIG. 8d).

In accordance with the present invention, the PRM (42) uses the first, the second and the third differentials of each of those four localized plantar pressure signals in order to determine the sensors' state. From there, the PRM (42) will be able to determine the phase of locomotion portion and portion of locomotion of the subject.

FIGS. 9a to 9d and 10a to 10d show examples of graphs of localized plantar pressures, as well as their first, second and third differentials, at the calcaneus and MP regions respectively, for a linear walking path of 109,5 steps/minute.

Figure 12A:
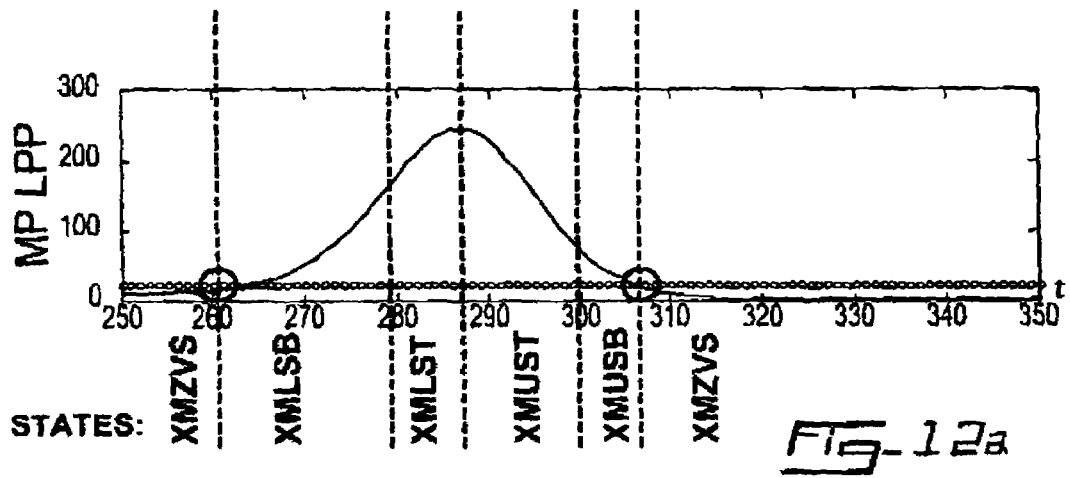
FIGS. 12a to 12c give an example of the states of a plantar pressure sensor with reference to the data signal and its three first differentiation for a plantar pressure sensor at the metatarsophalangeal (MP)region.
Figure 12B:
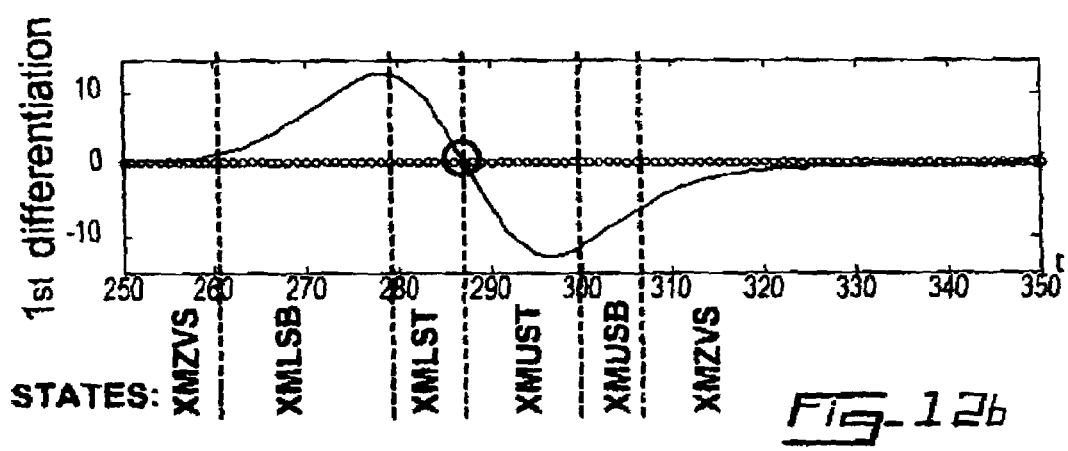
Figure 12C:
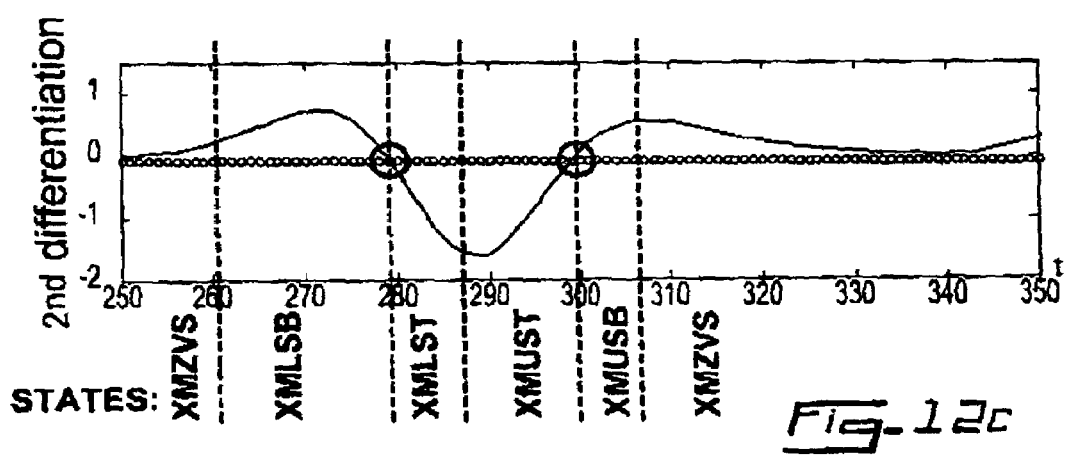

FIGS. 11a to 11d show graphically the state boundary conditions for a typical localized plantar pressure signal, and its first three differentials, at the calcaneous region, while FIGS. 12a to 12c do so for the localized plantar pressure signal, and its first two differentials, at the MP region. This shows the relationships between the various data and derivative signals, and the states.

In use, for the detection of the state of the four localized plantar pressures, denoted $f_{rx}$ where x=[1, 4], the PRM (42) uses a set of first state machines to select, at each increment in time, the current state of each sensor. For this purpose, the algorithm uses a set of events whose values define the conditions to pass from one state to another for each of the localized plantar pressures. Table 2 lists the events:

TABLE 2

List of events used to evaluate the state boundary condition of a localized plantar pressure

| Event | Acronym | Description |
|---|---|---|
| Non-Zero of $f_{rx}$ | $FR\_BIN_x$ | Detection of a positive $f_{rx}$ |
| First Differentiation of $f_{rx}$ | $FRfst\_BIN_x$ | Detection of positive first differentiation of $f_{rx}$ |
| Second Differentiation of $f_{rx}$ | $FRsec\_BIN_x$ | Detection of positive second differentiation of $f_{rx}$ |
| Third Differentiation of $f_{rx}$ | $FRtrd\_BIN_x$ | Detection of positive third differentiation of $f_{rx}$ |
| Static $f_{rx}$ | $STA\_BIN_x$ | Detection of a static evolution of all $f_{rx}$ |

The conditions placed on the values of each of the depicted events of Table 2 define when the state machines pass from one state to another for each of the localized plantar pressures. Table 3 lists the thresholds used to assess if the aforementioned conditions are met, in which $sum_y$ depicts the five complementary signals, for y=[a, e] as described in Table 4, while Table 5 shows the mathematical form of the events used to evaluate the state boundary condition of the localized plantar pressures.

TABLE 3

List of thresholds used to evaluate the state boundary condition of a localized plantar pressure

| Threshold | Acronym | Description |
|---|---|---|
| Positive value of $f_{rx}$ | $ZV\_FR_x$ | Threshold to consider $f_{rx}$ to be positive |
| Positive value of $\partial f_{rx}/\partial t$ | $ZV\_FRfst_x$ | Threshold to consider the first differentiation of $f_{rx}$ to be positive. |
| Positive value of $\partial^2 f_{rx}/\partial t^2$ | $ZV\_FRsec_x$ | Threshold to consider the second differentiation of $f_{rx}$ to be positive. |
| Positive value of $\partial^3 f_{rx}/\partial t^3$ | $ZV\_FRtrd_x$ | Threshold to consider the third differentiation of $f_{rx}$ to be positive. |
| Position value of $\partial sum_y/\partial t$ | $ZV\_SUMfst$ | Threshold to consider the absolute value of the first differentiation of $sum_y$ to be positive. |
| Positive value of $\partial^2 sum_y/\partial t^2$ | $ZV\_SUMsec$ | Threshold to consider the absolute value of the second differentiation of $sum_y$ to be positive |

TABLE 4

List of complementary signals built from the four localized plantar pressure $f_{r1}, f_{r2}, f_{r3}, f_{r4}$.

| Signal | Acronym | Description | Mathematical valu |
|---|---|---|---|
| Left foot | $sum_a$ | Localized plantar pressure signal of left foot | $(f_{r1} + f_{r2})/2$ |
| Right foot | $sum_b$ | Localized plantar pressure signal of right foot | $(f_{r3} + f_{r4})/2$ |
| Both calcaneus | $sum_c$ | Localized plantar pressure signal of both calcaneus | $(f_{r1} + f_{r3})/2$ |
| Both MP | $sum_d$ | Localized plantar pressure signal of both MP | $(f_{r2} + f_{r4})/2$ |
| Both feet | $sum_e$ | Localized plantar pressure signal of both feet | $(f_{r1} + f_{r2} + f_{r3} + f_{r4})/4$ |

TABLE 5

Mathematical formulation of events

| Acronym | Mathematical form |
|---|---|
| $FR\_BIN_x$ | $\begin{cases} 0 & \text{if } f_{r1}(k) < 2V\_FR_s \\ 1 & \text{otherwise} \end{cases}$ |

TABLE 5-continued

Mathematical formulation of events

| Acronym | Mathematical form |
|---|---|
| FRfst_BIN$_x$ | $\left\{ \begin{array}{l} 0 \text{ if } \frac{df_{rx}(k)}{d(k)} < ZV\_FRfst_s \\ 1 \text{ otherwise} \end{array} \right\}$ |
| FRsec_BIN$_x$ | $\left\{ \begin{array}{l} 0 \text{ if } \frac{d^2 f_{rx}(k)}{d^2(k)} < ZV\_FRfsec_s \\ 1 \text{ otherwise} \end{array} \right\}$ |
| FRtrd_BIN$_x$ | $\left\{ \begin{array}{l} 0 \text{ if } \frac{d^3 f_{rx}(k)}{d^3(k)} < ZV\_FRtrd_s \\ 1 \text{ otherwise} \end{array} \right\}$ |
| STA_BIN | $\left\{ \begin{array}{l} 0 \text{ if } \left( \left( \left| \frac{dsum_y(k)}{d(k)} \right| > ZV\_SUMfst \right) \| \left( \left| \frac{d^2 sum_y(k)}{d^2(k)} \right| > ZV\_SUMsec \right) \right) \forall\ y \\ 1 \text{ otherwise} \end{array} \right\}$ |

Figure 13:
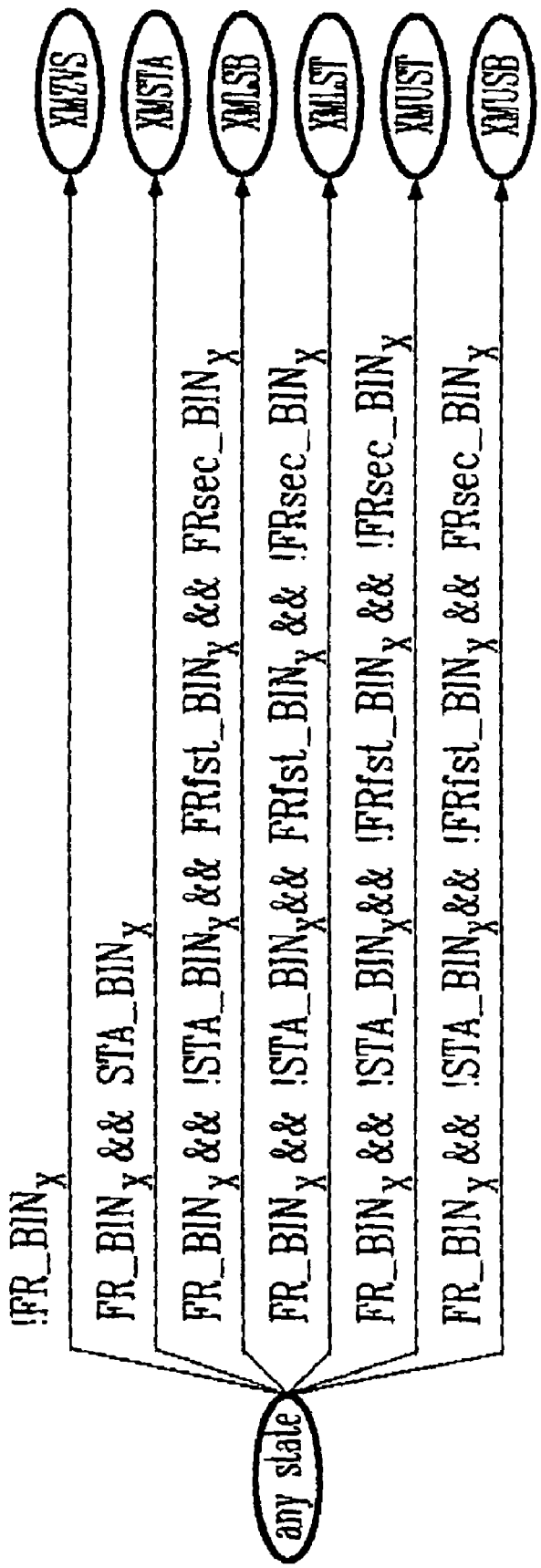
FIG. 13 is an example of a state machine diagram for the selection of the state of the plantar pressure sensors for the calcaneous region.
Figure 14:
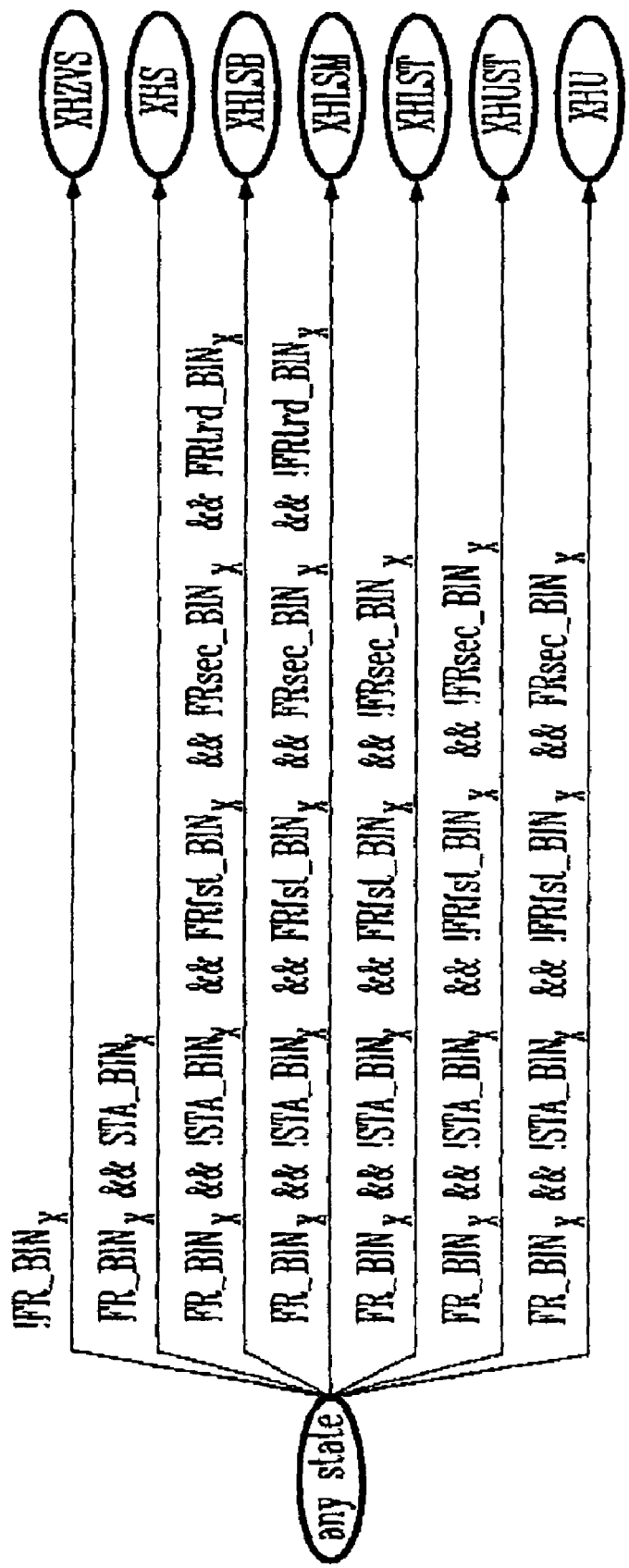
FIG. 14 is an example of a state machine diagram for the selection of the state of the plantar pressure sensors at the metatarsophalangeal (MP) region.

FIGS. 13 and 14 show, respectively, the diagrams of the state machines used for the detection of the state of the localized plantar pressure at the calcaneous and the MP regions, while Tables 6 and 7 summarize the state boundary conditions between the states of each localized plantar pressure.

TABLE 6

List of state boundary conditions defining the states of the main artificial proprioceptors at the calcaneus region

| CURRENT STATE | STATE BOUNDARY CONDITIONS | NEXT STATE |
|---|---|---|
| Any state | !FR_BIN$_x$ | XHZVS |
| Any state | FR_BIN$_x$ && STA_BIN$_x$ | XHSTA |
| Any state | FR_BIN, && !STA_BIN$_x$ && FRfst_BIN$_x$ && FRsec_BIN$_x$ && FRtrd_BIN$_x$ | XHLSB |
| Any state | FR_BIN$_x$ && !STA_BIN$_x$ && FRfst_BIN$_x$ && FRsec_BIN$_x$ && !FRtrd_BIN$_x$ | XHLSM |
| Any state | FR_BIN$_x$ && !STA_BIN$_x$ && FRfst_BIN$_x$ && !FRsec_BIN$_x$ | XHLST |
| Any state | FR_BIN$_x$ && !STA_BIN$_x$ && !FRfst_BIN$_x$ && !FRsec_BIN$_x$ | XHUST |
| Any state | FR_BIN$_x$ && !STA_BIN$_x$ && !FRfst_BIN$_x$ && FRsec_BIN$_x$ | XHUSB |

TABLE 7

List of state boundary conditions defining the states of the main artificial proprioceptors at metatarsophalangeal region

| CURRENT STATE | STATE BOUNDARY CONDITIONS | NEXT STATE |
|---|---|---|
| Any state | !FR_BIN$_x$ | XMZVS |
| Any state | FR_BIN$_x$ && STA_BIN$_x$ | XMSTA |
| Any state | FR_BIN$_x$ && !STA_BIN$_x$ && FRfst_BIN$_x$ && FRsec_BIN$_x$ | XMLSB |
| Any state | FR_BIN$_x$ && !STA_BIN$_x$ && FRfst_BIN$_x$ && !FRsec_BIN$_x$ | XMLST |
| Any state | FR_BIN$_x$ && !STA_BIN$_x$ && !FRfst_BIN$_x$ && !FRsec_BIN$_x$ | XMUST |
| Any state | FR_BIN$_x$ && !STA_BIN$_x$ && !FRfst_BIN$_x$ && FRsec_BIN$_x$ | XMUSB |

Figure 15:
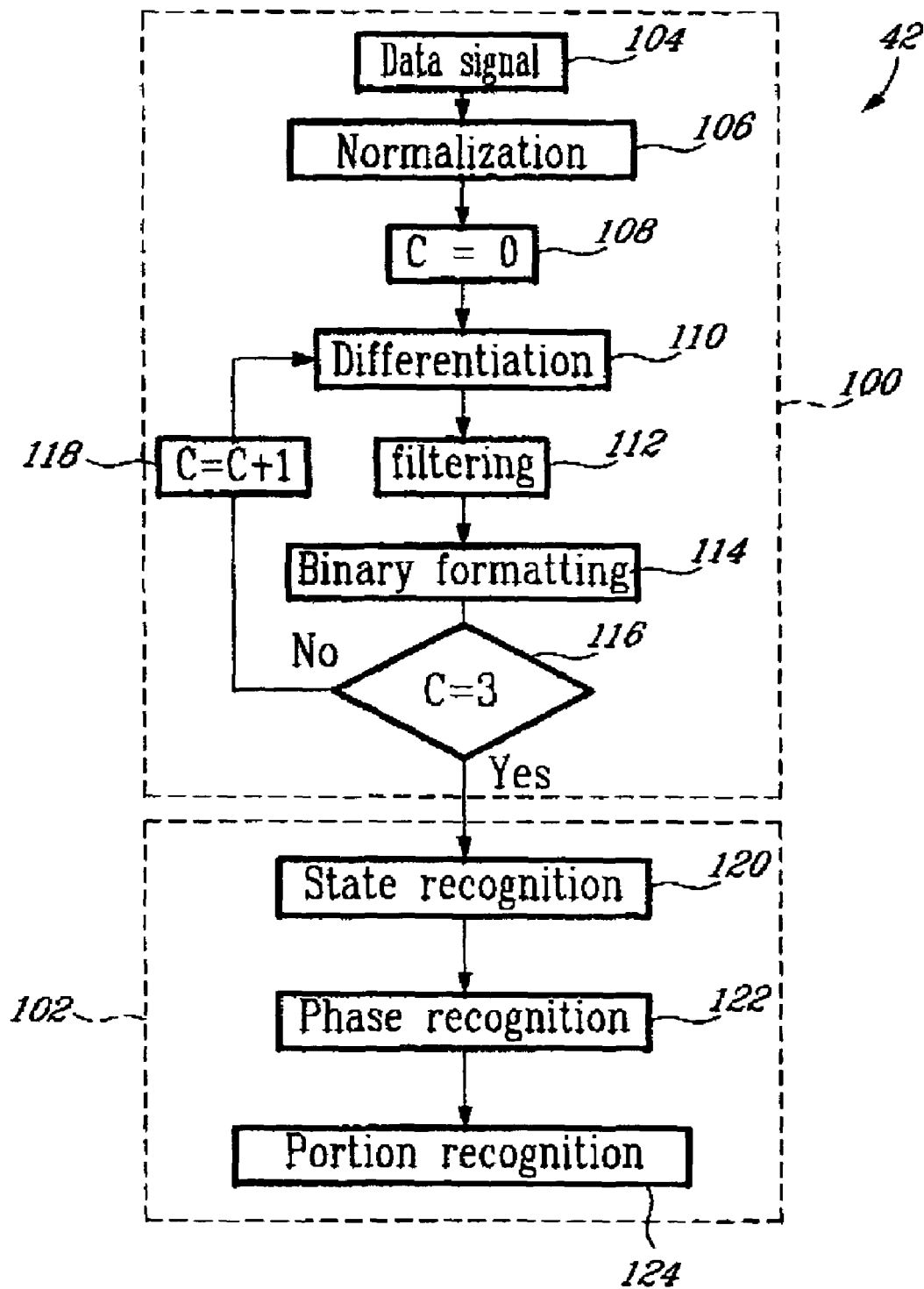
FIG. 15 is an overall block diagram of the Phase Recognition Module (PRM)

FIG. 15 shows a flow chart that depicts the PRM algorithm, which comprises two main parts, namely the pre-processing of the main artificial proprioceptors signals and the locomotion breakdown, illustrated by blocks 100 and 102 respectively. The sequence of steps performed the pre-processing of the main artificial proprioceptors signals, represented by block 100, is indicated by the sequence of blocks 104 to 118. At block 104, the four localized plantar pressures signals are received from the interface and normalized at block 106 using subject specific calibration values. The four normalized local plantar pressures then go through the pre-processing steps represented by blocks 104 to 118. At block 112, the four normalized local plantar pressures are filtered to reduce their spectral composition. A counter is then initialized at block 108, which in turn starts a loop comprising blocks 110 to 116. The first step of the loop, at block 110, consist in the differentiation of the signals. The signals resulting from the differentiation step are filtered at block 112, in order to limit the noise induced during the differential computation, and go through binary formatting at block 114. At block 116, the algorithm checks if the counter has reached 3 iterations. If so, the algorithm, having computed all first three derivatives of the four normalized local plantar pressures signals, exits the loop to block 102. If not, the algorithm proceeds to block 110 where the counter is increased at block 118 and the loop is repeated, in order to computed the next derivative, by proceeding to block 110. When the loop exists to block 102, the algorithm enters into the locomotion breakdown part of the algorithm. The sequence of steps performed by the locomotion breakdown, represented by block 102, is indicated by the sequence of blocks 120 to 124. From the four normalized local plantar pressures and their first three derivatives, block 120 determines the states of each sensor while blocks 122 and 124 determine the phase and the portion of locomotion, respectively.

The normalization step, represented by block 106, consists in levelling the magnitude of the raw data signals according to the anthropomorphic characteristics of the subject such as, in the preferred embodiment, the subject's weight. The raw data signals of the four localized plantar pressures are divided by the total magnitude provided by the four sensors during calibration and then provided as the normalized local plantar pressures to block 110.

At block 112 the normalized raw signals of the four localized plantar pressures and their first three differentials are numerically filtered to reduce their spectral composition, as well as to limit the noise induced during the derivative computation. The preferred embodiment of the PRM (42) uses a $2^{nd}$ order numerical filter in which the cut-off frequency, the damping factor and the forward shifting have been set, experimentally, to optimize the calculation according to the locomotion portion and the type of signal. The PRM (42) may use other types of numerical filters as well, for example a "Butterworth" filter, as long as the filter's dynamic is similar to the one provided by the $2^{nd}$ order filter shown thereafter for each locomotion portion. Equation 4 shows the mathematical relationships of the $2^{nd}$ order numerical filter which is implemented within the PRM (42). Table 8 provides examples of filtering parameters for three different portions of locomotion.

Laplace Form $$H(s) = \frac{\omega_n^2}{s^2 + 2\cdot\zeta\cdot\omega_n\cdot s + \omega_\mu^2}$$ Equation 3 where
$\omega_n$ in the nth damping natural frequency, $$\omega_n = \frac{\omega_x}{\sqrt{1-2\zeta^2}}, \zeta < 1$$

$\omega_r$ is called the resonance frequency for $\zeta<1$
$\zeta$ is the damping factor Recursive Form $$H(z) = \frac{b_2 z^{-1} + b_3 z^{-2}}{a_1 + a_2 z^{-1} + a_j 2^{-2}}$$ Equation 4

$a_1 y(k) = b_2 x(k-1) + b_3 x(k-2) - a_2 y(k-1) - a_3 y(k-2)$ where
$a_1 = 1$
$a_2 = -2\cdot\alpha\cdot\beta$
$a_3 = \alpha^2$
$b_1 = 0$ $$b_2 = 1 - \alpha\cdot\left[\beta + \frac{\zeta\cdot\omega_n\cdot\partial}{\omega_r}\right]$$

$$b_3 = \alpha^2 + \alpha\cdot\left[\frac{\zeta\cdot\omega_n\cdot\partial}{\omega_r} - \beta\right]$$

$\alpha = e^{-\zeta\cdot\omega_n T_e}$
$\beta = \cos(\omega_r T_e)$
$\partial = \sin(\omega_r T_e)$
$T_e$ = sampling rate

TABLE 8

Examples of parameters of $2^{nd}$ order filters used by the PRM

| Portion of locomotion | Type of signal | Filtering Parameters | | |
|---|---|---|---|---|
| | | Cut-Off Frequency ($F_c$) | Damping Factor (z) | Forward Shifting |
| Linear Walking - Beginning path (BTW) | Raw | 2 | 0.680 | 7 |
| | Derivative | 3 | 0.700 | 3 |
| Linear Walking - Cyclical path (CTW) | Raw | 2 | 0.680 | 7 |
| | Derivative | 3 | 0.700 | 3 |
| Linear Walking - Ending path (ETW) | Raw | 2 | 0.680 | 7 |
| | Derivative | 3 | 0.700 | 3 |

At block 110, the derivatives are obtained by the standard method consisting of numerically differentiating the current and the previous samples of localized plantar pressures.

The derivatives obtained at block 110 then go through binary formatting at block 114. The result of the binary formatting operation will be a "1" if the sign of the derivative is positive, "0" if it is negative. This step facilitates the identification of the sign changes of the differentiated signals as binary events.

At block 120, the PRM (42) determines the current state of each sensor using state machines such as the ones shown in FIGS. 13 and 14.

In the PRM (42), the states of the localized plantar pressures are preferably expressed as a 10-bit words in which each bit corresponds to a specific possible state. Tables 9 to 12 list the binary equivalents of each state of the localized plantar pressures at the calcaneous and the MP regions of the left and the right foot. Of course, words of different bit length may be used as well to represent the state of each localized plantar pressure.

TABLE 9

Numerical labels of the states for the localized plantar pressure at calcaneous area of the left foot

| STATE | BINARY LABEL | DECIMAL LABEL |
|---|---|---|
| LHSBS | 0 0 0 0 0 0 0 0 0 1 | 0 |
| LHLSB | 0 0 0 0 0 0 0 0 1 0 | 1 |
| LHLSM | 0 0 0 0 0 0 0 1 0 0 | 2 |
| LHLST | 0 0 0 0 0 0 1 0 0 0 | 3 |
| LHUST | 0 0 0 0 0 1 0 0 0 0 | 4 |
| LHUSM | 0 0 0 0 1 0 0 0 0 0 | 5 |
| LHUSB | 0 0 0 1 0 0 0 0 0 0 | 6 |
| LHZVS | 0 0 1 0 0 0 0 0 0 0 | 7 |
| LHSTA | 0 1 0 0 0 0 0 0 0 0 | 8 |

TABLE 10

Numerical labels of the states for the localized plantar pressure at metatarsaphalangeal area of the left foot

| STATE | BINARY LABEL | DECIMAL LABEL |
|---|---|---|
| LMSBS | 0 0 0 0 0 0 0 0 0 1 | 0 |
| LMLSB | 0 0 0 0 0 0 0 0 1 0 | 1 |
| LMLSM | 0 0 0 0 0 0 0 1 0 0 | 2 |
| LMLST | 0 0 0 0 0 0 1 0 0 0 | 3 |
| LMUST | 0 0 0 0 0 1 0 0 0 0 | 4 |
| LMUSM | 0 0 0 0 1 0 0 0 0 0 | 5 |
| LMUSB | 0 0 0 1 0 0 0 0 0 0 | 6 |
| LMZVS | 0 0 1 0 0 0 0 0 0 0 | 7 |
| LHSTA | 0 1 0 0 0 0 0 0 0 0 | 8 |

TABLE 11

Numerical labels of the states for the localized plantar pressure at calcaneous area at the right foot

| STATE | BINARY LABEL | DECIMAL LABEL |
|---|---|---|
| RHSBS | 0 0 0 0 0 0 0 0 0 1 | 0 |
| RHLSB | 0 0 0 0 0 0 0 0 1 0 | 1 |
| RHLSM | 0 0 0 0 0 0 0 1 0 0 | 2 |
| RHLST | 0 0 0 0 0 0 1 0 0 0 | 3 |
| RHUST | 0 0 0 0 0 1 0 0 0 0 | 4 |
| RHUSM | 0 0 0 0 1 0 0 0 0 0 | 5 |
| RHUSB | 0 0 0 1 0 0 0 0 0 0 | 6 |
| RHZVS | 0 0 1 0 0 0 0 0 0 0 | 7 |
| RHSTA | 0 1 0 0 0 0 0 0 0 0 | 8 |

TABLE 12

Numerical labels of the states for the localized plantar pressure at metatarsophalangeal area of the right foot

| STATE | BINARY LABEL | DECIMAL LABEL |
|---|---|---|
| RMSBS | 0 0 0 0 0 0 0 0 0 1 | 0 |
| RMLSB | 0 0 0 0 0 0 0 0 1 0 | 1 |
| RMLSM | 0 0 0 0 0 0 0 1 0 0 | 2 |
| RMLST | 0 0 0 0 0 0 1 0 0 0 | 3 |
| RMUST | 0 0 0 0 0 1 0 0 0 0 | 4 |
| RMUSM | 0 0 0 0 1 0 0 0 0 0 | 5 |
| RMUSB | 0 0 0 1 0 0 0 0 0 0 | 6 |
| RMZVS | 0 0 1 0 0 0 0 0 0 0 | 7 |
| RHSTA | 0 1 0 0 0 0 0 0 0 0 | 8 |

At block 122, the PRM (42) generates the phase, which is preferably expressed as the direct binary combination of the states of the four localized plantar pressures. Accordingly, the phase can be represented by a 40-bit word wherein the lower part of the lower half word, the higher part of the lower half word, the lower part of the higher half word and the higher part of the higher half word correspond, respectively, to the calcaneous area of the left foot, the MP area of the left foot, the calcaneous area of the right foot and the MP area of the right foot, as represented in Tables 9 to 12. Table 13 presents an example of the identification of a phase from the states of the four localized plantar pressures.

TABLE 13

Identification of a phase from the states of the main artificial proprioceptors

| State of Localized Plantar Pressure | | | | |
|---|---|---|---|---|
| Right Foot | | Left Foot | | |
| MP area | Calcaneous | MP area | Calcaneous | Corresponding Phase |
| 0000000100 | 0000010000 | 0000000001 | 0000010000 | 00000001000000010000 00000000010000010000 |

At block 124, the PRM (42) selects the portion of locomotion the subject is currently using the state machine shown in FIG. 6. Each portion of locomotion is composed of a sequence of phases.

Accordingly, Table 14 presents the phases sequence mapping for the Beginning Path of Linear Walking (BTW) locomotion portion corresponding to FIG. 7. This table shows the label, the decimal value and as well the phase boundary conditions of each phase.

TABLE 14

Example of phases sequence mapping for the locomotion portion labeled "Beginning Path of Linear Walking" (BTW)

| Phase | | Phase Boundary Conditions | | | |
|---|---|---|---|---|---|
| Label | Value | $F_{r1}$ | $F_{r2}$ | $F_{r3}$ | $F_{r4}$ |
| BTW_1 | 275146604800 | 8 | 8 | 8 | 8 |
| BTW_2 | 34493964416 | 5 | 7 | 3 | 7 |
| BTW_3 | 2281717888 | 1 | 7 | 4 | 7 |
| BTW_4 | 4429217920 | 2 | 7 | 5 | 7 |
| BTW_5 | 17213489280 | 4 | 5 | 6 | 7 |
| BTW_6 | 17314119808 | 4 | 7 | 5 | 7 |
| BTW_7 | 34493988992 | 5 | 7 | 5 | 7 |
| BTW_8 | 34494087296 | 5 | 7 | 7 | 7 |
| BTW_9 | 34361868416 | 5 | 1 | 5 | 7 |
| BTW_10 | 34361966720 | 5 | 1 | 7 | 7 |
| BTW_11 | 68723802240 | 6 | 2 | 7 | 7 |
| BTW_12 | 68727996544 | 6 | 3 | 7 | 7 |
| BTW_13 | 68727867520 | 6 | 3 | 1 | 7 |
| BTW_14 | 137455732864 | 7 | 4 | 1 | 7 |
| BTW_15 | 137455734912 | 7 | 4 | 2 | 7 |
| BTW_16 | 137455739008 | 7 | 4 | 3 | 7 |
| BTW_17 | 137472512128 | 7 | 5 | 2 | 7 |
| BTW_18 | 137472516224 | 7 | 5 | 3 | 7 |
| BTW_19 | 137472524416 | 7 | 5 | 4 | 7 |
| BTW_20 | 137573187712 | 7 | 7 | 4 | 7 |
| BTW_21 | 137573204096 | 7 | 7 | 5 | 7 |
| BTW_22 | 137573187586 | 7 | 7 | 4 | 1 |
| BTW_33 | 137573203970 | 7 | 7 | 5 | 1 |
| BTW_24 | 137573236740 | 7 | 7 | 6 | 2 |
| BTW_25 | 137573236744 | 7 | 7 | 6 | 3 |

Table 15 enumerates a sample of boundary conditions associated with the locomotion portion of the sitting and typical walking on flat ground movements, while Table 3 lists the thresholds used to assess if the aforementioned conditions are met.

TABLE 15

Example of a list of portion boundary conditions defining specific locomotion portions such as sitting movements (STA-SUP-SIT-SDW-STA locomotion portion) and typical waking on flat ground (STA-BTW-CTW-ETW-STA locomotion portion)

| Current Portion | Set of Events | Next Portion |
|---|---|---|
| STA | $SWING_{leg}$ | BTW |
| | $!STATIC\_GR_{leg} \parallel$ | |
| | $!STATIC\_GR_{prost}$ | |
| | $FR\_LOW_{prost\_heel}$ | |
| | $FR\_BIN_{leg\_heel}$ | |
| | BTW_SWING | |
| | $FR\_HIGH_{leg\_heel}$ | SDW |
| | $FR\_HIGH_{prost\_heel}$ | |
| | PKA_SDW | |
| BTW | $STATIC\_GR_{leg}$ | ETW |
| | $STATIC\_GR_{prost}$ | |
| | $SUM\_BIN_{prost}$ | CTW |
| | $SWING_{prost}$ | |
| CTW | $STATIC\_GR_{leg}$ | STA |
| | $STATIC\_GR_{prost}$ | |
| | $FR\_BIN_{prost\_heel}$ | ETW |
| | $FR\_BIN_{leg\_heel}$ | |
| | PKA_ETW | |
| | $STATIC\_GR_{leg} \parallel STATIC\_GR_{prost}$ | |
| ETW | PKA_STA | STA |
| SDW | PKA_SIT | SIT |
| | PKA_STA | STA |
| SIT | $GR\_POS_{leg}$ | SUP |
| | MIN_SIT | |
| | $FR\_HIGH_{leg\_mp}$ | |
| | $FR\_HIGH_{prost\_mp}$ | |
| | PKA_STA | STA |
| SUP | $!SUM\_BIN_{prost}$ | SIT |
| | $!SUM\_BIN_{leg}$ | |
| | PKA_STA | STA |
| | !PKA_SUP_RAMP | SIT |

TABLE 16

Example of a list of events used to evaluate the portion boundary conditions defining specific locomotion portions such as sitting movements (STA-SUP-SIT-SDW-STA locomotion portion) and typical waking on flat ground (STA-BTW-CTW-ETW-STA locomotion portion)

| Event | Acromyn | Description |
|---|---|---|
| Swing occurence | $SWING_y$ | Detection of a swing prior to a foot strike |
| Non-Zero of $f_{rx}$ | $FR\_BIN_x$ | Detection of a positive $f_{rx}$ |
| Low $f_{rx}$ | $FR\_LOW_x$ | Detection of $f_{rx}$ level between the zero envelope and the STA envelope |
| High $f_{rx}$ | $FR\_HIGH_x$ | Detection of $f_{rx}$ level above the STA envelope |
| Static $g_{ry}$ | $STATIC\_GR_y$ | Detection of $g_{ry}$ level below the zero angular speed envelope and the zero acceleration envelope |
| Non-Zero of $sum_y$ | $SUM\_BIN_y$ | Detection of a positive $sum_y$ |
| BTW swing occurrence | BTW_SWING | Detection of typical walking $g_{r\_leg}$ during leg swing |
| Positive $g_{ry}$ | $GR\_POS_y$ | Detection of a positive $g_{ry}$ |
| Minimum sitting | MIN_SIT | Detection of a minimum time in portion SIT |

TABLE 16-continued

Example of a list of events used to evaluate the portion boundary
conditions defining specific locomotion portions such as sitting movements
(STA-SUP-SIT-SDW-STA locomotion portion) and typical waking on flat ground
(STA-BTW-CTW-ETW-STA locomotion portion)

| Event | Acromyn | Description |
|---|---|---|
| Sit down knee angle | PKA_SDW | Detection of knee angle higher than the STA envelope |
| End walking knee angle | PKA_ETW | Detection of knee angle lower than the STA envelope |
| Stance knee angle | PKA_STA | Detection of knee angle lower than the STA envelope |
| Sit down knee angle | PKA_SIT | Detection of knee angle higher than the SIT envelope |
| Standing up knee angle | PKA_SUP_RAMP | Detection of standing up knee angle evolution | where
X stands for leg_heel, leg_mp, prosthetic_heel or prosthetic_mp
Y stands for leg or prosthesis The normalization step of block 106 uses specific calibration values. These values are computed the first time a subject uses the actuated prosthesis (12) or at any other time as may be required. Two calibration values are preferably used: the zero calibration value and the subject's weight calibration value. The zero calibration value consists in the measurement of the four localized plantar pressures when no pressure is applied to the sensors, while the subject's weight calibration value is the subject's weight relative to the magnitude of the total response of the sensors.

Figure 16:
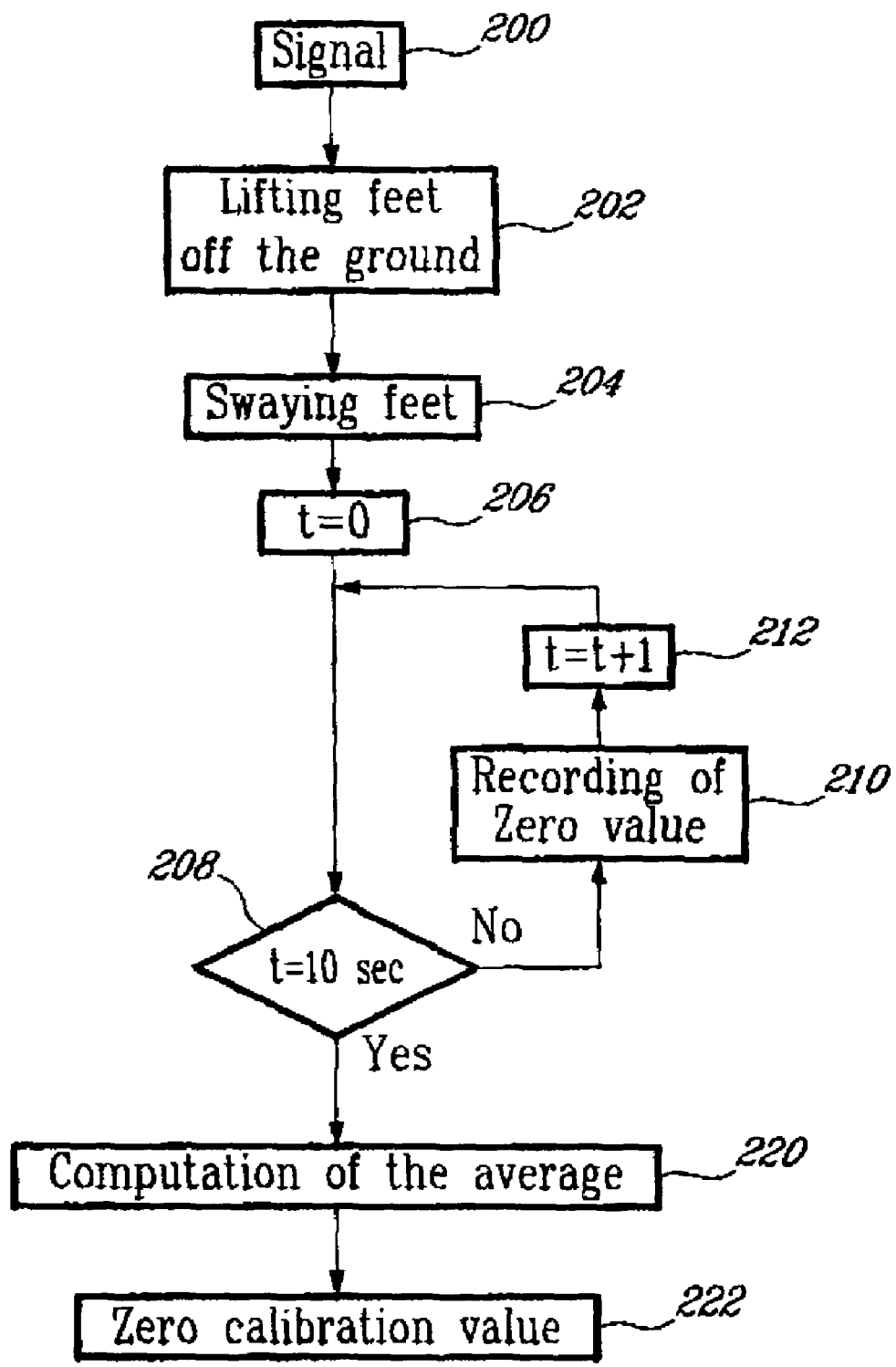
FIG. 16 is a block diagram showing the zero calibration.

The algorithm to obtain the zero calibration value of the sensors is depicted by the flow chart shown in FIG. 16. The sequence of steps composing the algorithm is indicated by the sequence of blocks 200 to 222. In block 200, the algorithm starts with the four localized plantar pressures. At block 202, the subject sits on a surface high enough such that his feet hang freely in the air. Then, at block 204, the subject lightly swings his feet back and forth, which initialises a timer at block 206, which in turn starts a loop comprising blocks 208, 210 and 212. At block 208, the algorithm checks if the timer has reached 10 seconds, if so, then the algorithm exits the loop to block 220, if not, the algorithm proceeds to block 210 and records the zero value of the four sensors. Then, at block 212, the timer is increased and the loop is repeated by proceeding to block 208. At block 220, the average of each localized plantar pressures is computed and finally provided as the zero calibration value at block 222.

Figure 17:
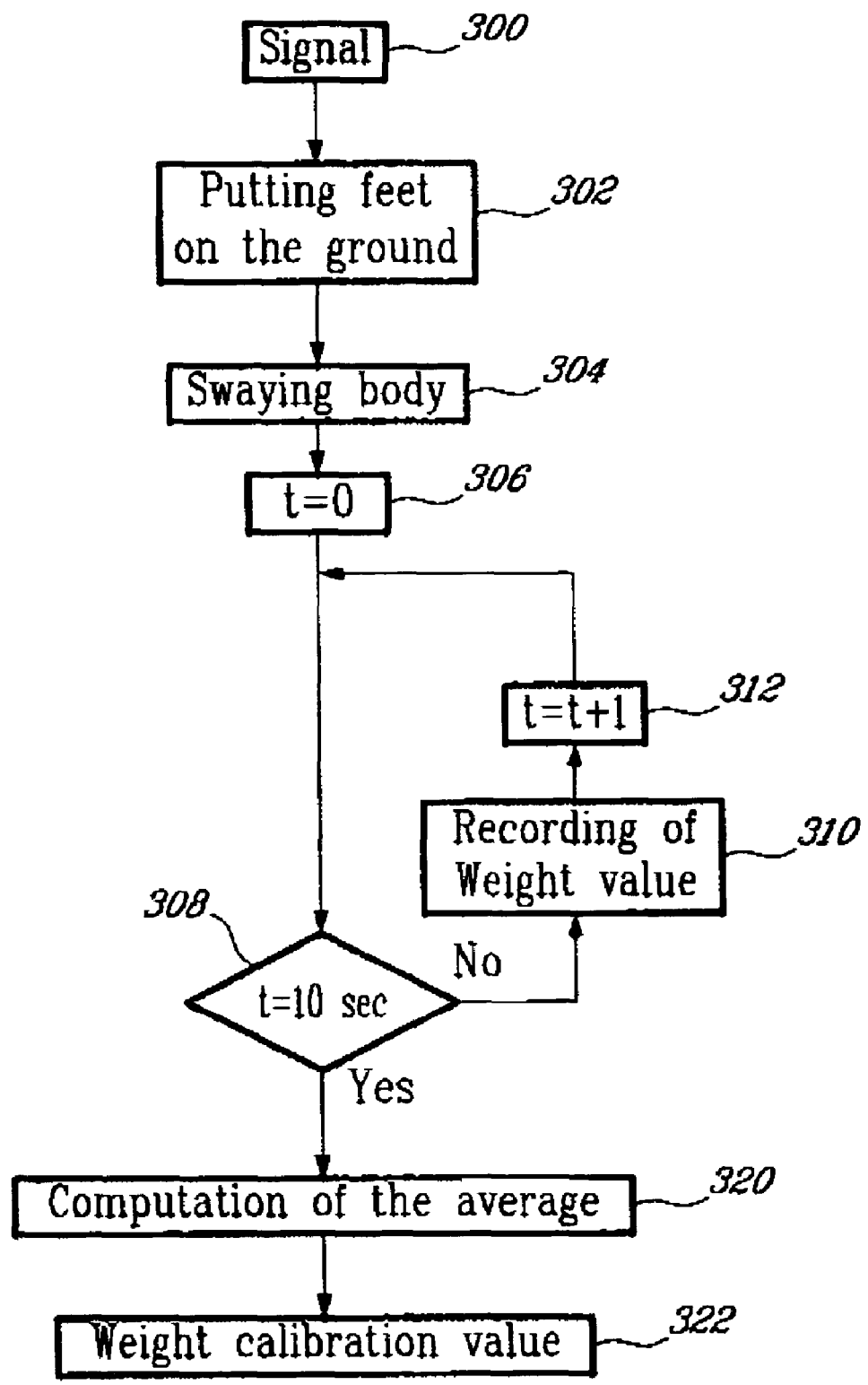
FIG. 17 is a block diagram showing the subject's weight calibration.

In a similar fashion, the algorithm to obtain the subject's weight calibration value is depicted by the flow chart shown in FIG. 17. The sequence of steps composing the algorithm is indicated by the sequence of blocks 300 to 322. In block 300, the algorithm starts with the four localized plantar pressure. At block 302, the subject stands up in a comfortable position, feet at shoulder width distance, while maintaining the body in the stance position. Then, at block 304, the subject slowly swings back and forth and then left to right, which initialises a timer at block 306, which in turn starts a loop comprising blocks 308, 310 and 312. At block 308, the algorithm checks if the timer has reached 10 seconds, if so, then the algorithm exits the loop to block 320, if not, the algorithm proceeds to block 310 and records the subject's weight relative to the magnitude of the total response of the sensors. Then, at block 312, the timer is increased and the loop is repeated by proceeding to block 308. At block 320, the average of each localized plantar pressure is computed and finally provided as the weight calibration value at block 322.

Figure 18:
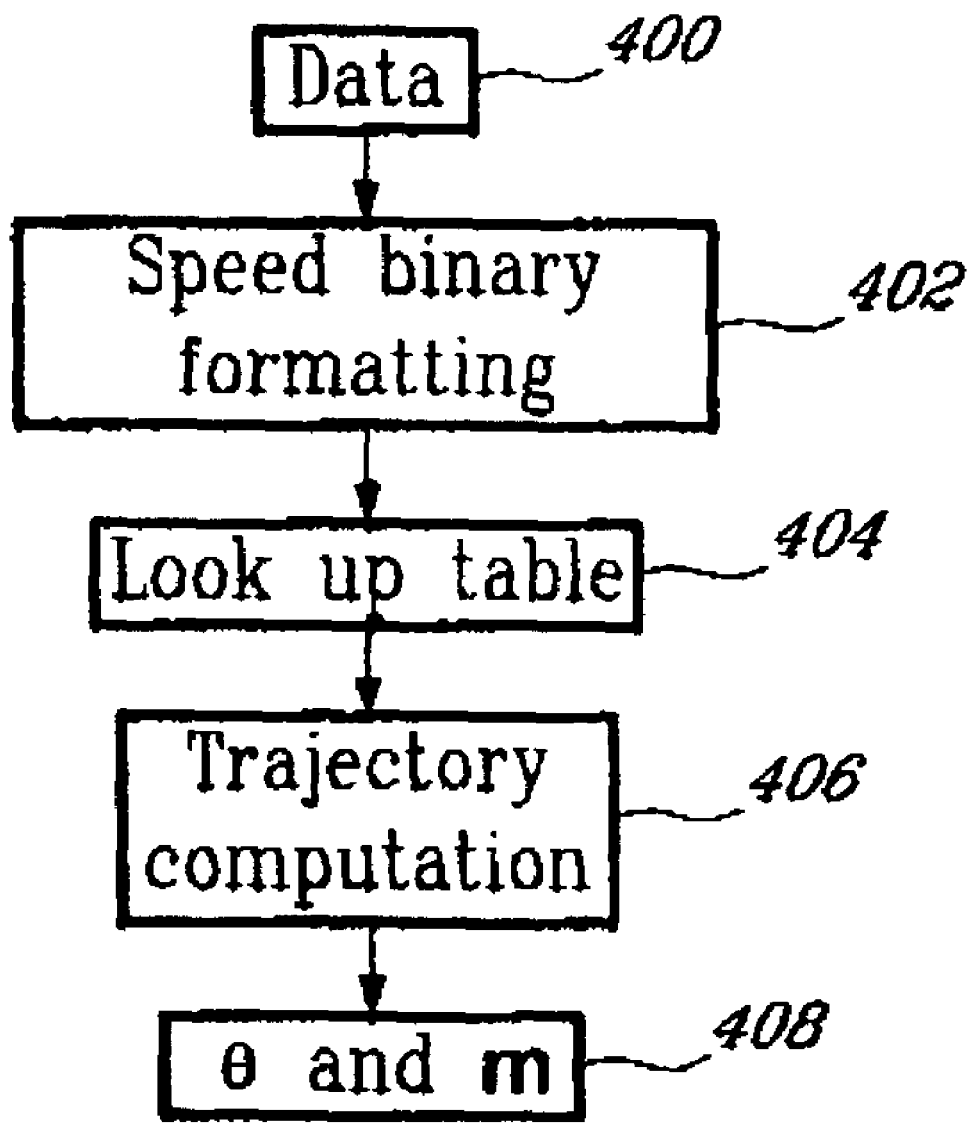
FIG. 18 is a block diagram of the Trajectory Generator (TG)

FIG. 18 shows a flow chart that depicts the TG algorithm used to establish a relationship, in real-time, between the output of the PRM (42) and localized plantar pressures and the knee joint trajectory. The sequence of steps composing the algorithm is indicated by the sequence of blocks 400 to 408. At block 400, the algorithm receives the normalized localized plantar pressures, the phase of locomotion portion and the portion of the locomotion from the PRM (42). Then, at block 402, the walking speed of the subject, in steps per minute, is obtained from computing the number of frames between two heel strikes, while taking into account the sampling frequency, and is binary formatted. More specifically, the subject's speed estimate $\hat{x}_v[k]$ (steps/minute) is obtained from computing the number of frames between two heel strikes $s_{heel}[k]$ (frames/step):

$$\hat{x}_v = 60 \frac{f_s}{s_{heel}[k] - s_{heel}[k-1]} \qquad \text{Equation 5}$$

where $f_s$ is the frame sampling frequency (frames/second).

A heel strike event occurs when:

$$\text{THRESHOLDHEELLOADING} < f_{ri_j}[k] - f_{ri_j}[k-1],$$
$$i_j = 1,3 \qquad \text{Equation 6}$$

At block 404, the algorithm uses the normalized localized plantar pressures, the phase of locomotion portion, the portion of the locomotion and the subject's speed in binary format to identify a set of linear normalized static characteristics linking the knee joint kinetic/kinematic parameters with the subject's locomotion in a lookup table. At block 406 the TG (44) comprises two transformation functions which compute the kinetic/kinematic parameters at time k, which are the angular displacement $\theta_{kn}(k)$ and the moment of force (torque) $m_{kn}(k)$, using the localized plantar pressures and their corresponding mathematical relationships (time-dependant equations and static characteristics) identified at block 404. The values of the kinetic/kinematic variables are then provided to the REG (48) at block 408.

The transformation functions used by the TG (44) at block 406 may generally be represented by a system of equations such as:

$$\theta_{g,h}(k) = \Omega_1(\partial_1(k),\chi(k),v(k)) + \Omega_2(\partial_2(k),\chi(k),v(k)) + \ldots$$
$$+ \Omega_{q-1}(\partial_{q-1}(k),\chi(k),v(k)) + \Omega_q(\partial_q(k),\chi(k),v(k)) \qquad \text{Equation 7}$$

$$m_{g,h}(k)=M_1(\partial_1(k),\chi(k),v(k))+M_2(\partial_2(k),\chi(k),\chi(k))+ \ldots \\ +M_{q-1}(\partial_{q-1}(k),\chi(k),v(k))+M_q(\partial_q(k),\chi(k),v(k))$$ Equation 8 where

- g=[sagittal (sg), frontal (fr), transversal (tr)] is the plane of the motion
- h=[hip (hp), knee (kn), ankle (an), metatarsophalangeal (mp)] is the joint
- q is the number of the main artificial proprioceptors' sensors
- $\partial_q$ is the phenomenological entity related to the locomotion and provided by the main artificial proprioceptors' sensors
- $\Omega_q$ is the transformation function between the phenomenological entity related to the locomotion, the kinematic variables of the lower extremities and the time
- $M_q$ is the transformation function between the phenomenological entity related to the locomotion, the kinetic variables of the lower extremities and the time
- $\partial_q$ is the phenomenological entity related to the locomotion and provided by the main artificial proprioceptors' sensors
- $\chi(k)=\Omega(p_h(k),p_r(k),v(k))$ is the state of the whole system (amputee and the AAP) in which k is the current increment
- $p_h(k)$ is the phase of the respective locomotion portion
- $p_r(k)$ is the locomotion portion
- v(k) is the walking speed
- k is the current increment In the case where the TG (44) uses polynomial relationships of order n, Equation 7 and Equation 8 become:

$$\theta_{g,h}(k)=a_{1,1}(\chi(k),v(k))\cdot\partial_1(k)+ \ldots +a_{1,n}(\chi(k),v(k))\cdot\partial_1 \\ (k)^n+a_{2,1}(\chi(k),v(k))\cdot\partial_2(k)+ \ldots +a_{2,n}(\chi(k),v(k))\cdot\partial_2 \\ (k)^n+ \ldots +a_{q-1,1}(\chi(k),v(k))\cdot\partial_{q-1}(k)+ \ldots +a^{q-1,n} \\ (\chi(k),v(k))\cdot\partial_{q-1}(k)^{n+\ldots+}a_{q,1}(\chi(k),v(k))\cdot\partial_q \\ (k)+ \ldots +a_{q,n}(\chi(k),v(k))\cdot\partial_q(k)^n$$ Equation 9

$$m_{g,h}(k)=b_{1,1}(\chi(k),v(k))\cdot\partial_1(k)+ \ldots +b_{1,n}(\chi(k),v(k))\cdot\partial_2 \\ (k)^n+b_{2,1}(\chi(k),v(k))\cdot\partial_2(k)+ \ldots +b_{2,n}(\chi(k),v(k))\cdot\partial_2 \\ (k)^n+ \ldots +b_{q-1,1}(\chi(k),v(k))\cdot\partial_{q-1}(k)+ \ldots +b_{q-1,n} \\ (\chi(k),v(k))\cdot\partial_{q-1}(k)^n+ \ldots +b_{q,1}(\chi(k),v(k))\cdot\partial_q \\ (k)+ \ldots +b_{q,n}(\chi(k),v(k))\cdot\partial_q(k)^n$$ Equation 10 where $a_{i,j}(\chi(k))$ and $b_{i,j}(\chi(k))$ i=1→q are the coefficients for the state $\chi(k)$ of the whole system and the walking speed v(k) and n is the order of the polynomial The preferred embodiment uses four localized plantar pressures, thus Equation 9 and Equation 10 become:

$$\theta_{g,h}(k)=a_{1,1}(\chi(k),v(k))\cdot f_{r1}(k)+ \ldots +a_{1,n}(\chi(k),v(k))\cdot f_{r1} \\ (k)^n+a_{2,1}(\chi(k),v(k))\cdot f_{r2}(k)+ \ldots +a_{2,n}(\chi(k),v(k))\cdot \\ f_{r2}(k)^n+a_{3,1}(\chi(k),v(k))\cdot f_{r3}(k)+ \ldots +a_{3,n} \\ (\chi(k),v(k))\cdot f_{r3}(k)^n+a_{4,1}(\chi(k),v(k))\cdot f_{r3}(k)+ \ldots + \\ a_{4,n}(\chi(k),v(k))\cdot f_{r3}(k)^n$$ Equation 11

$$m_{g,h}(k)=b_{1,1}(\chi(k),v(k))\cdot f_{r1}(k)+ \ldots +b_{1,n}(\chi(k),v(k))\cdot f_{r1} \\ (k)^n+b_{2,1}(\chi(k),v(k))\cdot f_{r2}(k)+ \ldots +b_{2,n}(\chi(k),v(k))\cdot \\ f_{r2}(k)^n+b_{3,1}(\chi(k),v(k))\cdot f_{r3}(k)+ \ldots +b_{3,n}(\chi(k),v \\ (k))\cdot f_{r3}(k)^n+b_{4,1}(\chi(k),v(k))\cdot f_{r3}(k)+ \ldots +b_{4,n}(\chi(k), \\ v(k))\cdot f_{r3}(k)^n$$ Equation 12 where $a_{i,j}(\chi(k))$ and $b_{i,j}(\chi(k))$ i=1→q are the coefficients for the state $\chi(k)$ of the whole system and the walking speed v(k) and n is the order of the polynomial Since all the kinetic/kinematic parameters $\theta_{kn}(k)$ and $m_{kn}(k)$ are computed from non complex mathematical relationships, the computation of the trajectory is simple and fast and can be calculated by a non-sophisticated electronic circuit board.

Figure 19:
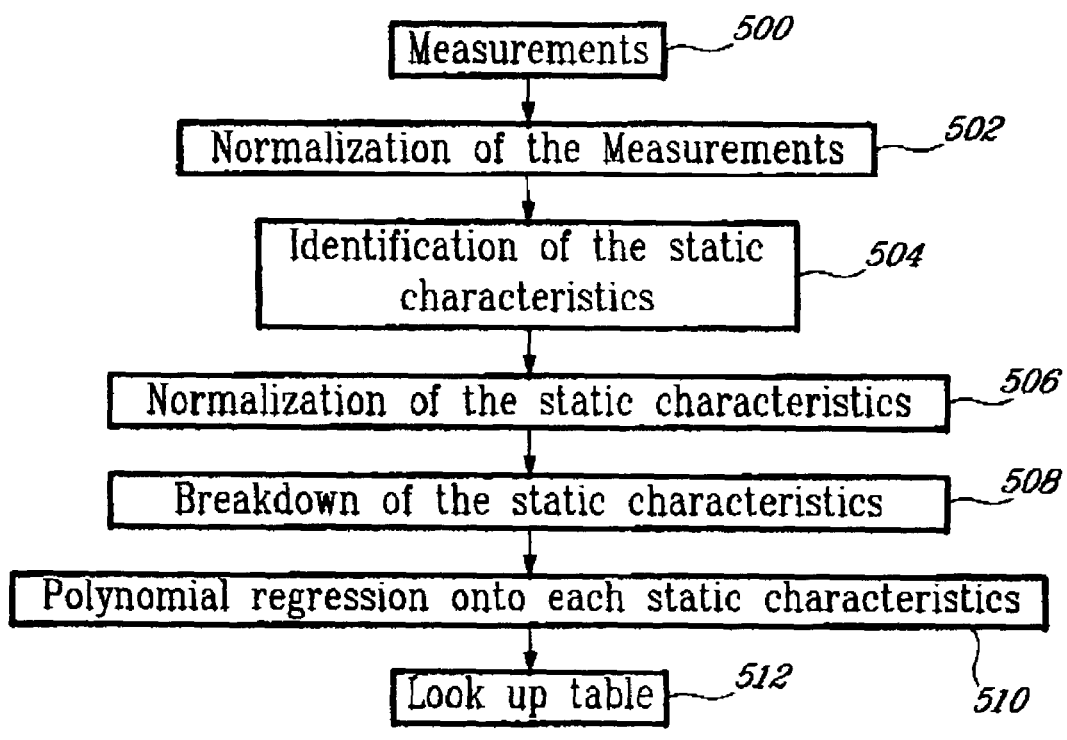
FIG. 19 is a block diagram showing the creation of the Trajectory Generator (TG) lookup table.

The mathematical relationships (time-dependant equations and static characteristics) used in these non complex mathematical relationships are contained in a lookup table referenced at block 404. FIG. 19 shows a flow chart that depicts the algorithm used to create the TG lookup table. The sequence of steps composing the algorithm is indicated by the sequence of blocks 100 to 512. At block 100, the algorithm measures the selected phenomelogical parameters, which in the preferred embodiment are the localized plantar pressures, and the kinetc/kinematic parameters $\theta_{kn}(k)$ and $m_{kn}(k)$ of a subject. The measured phenomelogical parameters are then normalized in function of the subject's weight. At block 104, the static characteristics linking the phenomelogical parameters to the kinetc/kinematic parameters and the time-dependant equations linking to the time are identified and are then normalized at block 106. Then at block 108, the mathematical relationships (time-dependant equations and static characteristics) are broken down according to the phenomelogical parameters, the phases of locomotion portion, portions of locomotion, the speed of the subject and in the case were Equation 11 and Equation 12 are linear functions, the binary formatted data signals. For each set of mathematical relationships (time-dependant equations and static characteristics) created by the breakdown, a polynomial regression is applied, at block 510, to the mathematical relationships (time-dependant equations and static characteristics) contained in the set. Finally, at block 512, the results of the polynomial regressions are stored in the lookup table and are indexed according to the breakdown of block 108.

The method for building this TG lookup table depicted by the flow chart of FIG. 19 may be applied to any equations belonging to the following analytical/logical family of functions:

$$y_{g,h} = a_0 + a_1 x_1 + a_2 x_1^2 + \cdots + a_n x_1^n + \\ b_0 + b_1 x_2 + b_2 x_2^2 + \cdots + b_m x_2^n + \\ \ldots \\ \beta_0 + \beta_1 x_x + \beta_2 x_x^2 + \cdots + \beta_\eta x_x^\eta$$

$$y_{g,h} = \sum_{i=0}^{n} a_i x_1^i + \sum_{i=0}^{m} b_i x_2^i + \ldots \sum_{i=0}^{\eta} \beta_i x_x^i$$

$$y_{g,h} = \sum_{i=0}^{n_1} a_{1,i} x_1^i + \sum_{i=0}^{n_2} a_{2,i} x_2^i + \ldots \sum_{i=0}^{n_x} a_{\chi,i} x_\chi^i$$

$$y_{g,h} = \sum_{j=1}^{\chi} \sum_{i=0}^{n_x} a_{j,i} \cdot x_j^i$$ Equation 13 where

- $y_{g,h}$ is the estimated kinematic ($\hat{\theta}_{g,h}$) or kinetic ($\hat{m}_{g,h}$) variables for the g lower extremities joint through the h plane of motion
- g is the lower extremities joint among the following set: hip, knee, ankle and metatarsophalangeal
- h is the plane of motion among the following set: sagittal, frontal and transversal
- $x_j$ is the $j^{th}$ locomotion related phenomenon, for example the $j^{th}$ localized plantar pressure
- $a_{j,i}$ is the $i^{th}$ coefficient associated the $j^{th}$ locomotion related phenomenon denoted $x_j$
- $n_j$ is the order of the polynomial depicting the $j^{th}$ locomotion related phenomenon denoted $x_j$
- $\chi$ is the number of locomotion related phenomena If it is considered that the family of functions in Equation 13 are dependant on the state of the system they depict, thus following system of equations is obtained:

$$y_{g,h} = \sum_{j=1}^{\chi} \sum_{i=0}^{n_x} a_{j,i}(x) \cdot x_j^i \qquad \text{Equation 14}$$

where x is the time dependant state vector of the system

In the preferred embodiment, $x_j$ may be substituted by the localized plantar pressures denoted $f_{r_i}$, where $i_f=[1, \chi]$. In the case of time-dependant equations, $x_j$ may be substituted by the time. Thus, in the case of plantar pressures, Equation 14 becomes:

$$y_{g,h} = \sum_{i_f=1}^{\chi} \sum_{i=0}^{n_{i,f}} a_{i_i,1}(x) \cdot f_{r_{i_f}}^i \qquad \text{Equation 15}$$

where x is the time dependant state vector of the system

Previously, $y_{g,h}$ has been defined as the estimated kinematic ($\hat{\theta}_{g,h}$) or kinetic ($\hat{m}_{g,h}$) variable for the g lower extremities joints through the h plan of motion. Thus, Equation 15 may be written as:

$$\hat{\theta}_{g,h} = \sum_{i_f=1}^{\chi} \sum_{i=0}^{n_{i_f}} a_{i_f,i}(x) \cdot f_{r_{i_f}}^i \qquad \text{Equation 16}$$

or $$\hat{m}_{g,h} = \sum_{i_f=1}^{\chi} \sum_{i=0}^{n_{i_f}} a_{i_f,i}(x) \cdot f_{r_{i_f}}^i \qquad \text{Equation 17}$$

The goal is the identification of the Equation 16 and Equation 17 functions from a set of $n_s$ samples, obtained from experimentation. A sample contains data related to the locomotion related phenomenon along with the corresponding kinematic ($\theta_{g,h}$) or kinetic ($m_{g,h}$) variables.

The following array of data is obtained from experimentation:

TABLE 16

Data obtained from experimentation

| t | x | $x_1$ | $x_2$ | ... | $x_j$ | ... | $x_\chi$ | $\theta_{g,n}$ | $m_{g,h}$ |
|---|---|---|---|---|---|---|---|---|---|
| 1 | | | | | | | | | |
| 2 | | | | | | | | | |
| ... | | | | | . | | | | |
| | | | | | . | | | | |
| $i_s$ | | | | ... | $x_{j,1}$ | ... | | | |
| ... | | | | | . | | | | |
| | | | | | . | | | | |
| $n_s$ | | | | | | | | | | where $j,\chi$ is the index and the number of locomotion related phenomena $i_s, n_s$ is the index and the number of frames t is the time [s]

x is the time dependant state vector of the system $x_j$ is the selected locomotion related phenomenon $\theta_{g,h}$ is the kinematic variables for the g lower extremities joint through the h plan of motion $m_{g,h}$ is the kinetic variable for the g lower extremities joint through the h plan of motion The logical functions $a_{j,i}(x)$ are then presented in the form of a look-up table, as shown in the following example:

TABLE 17

Look-up table example $a_{j,i}(x)$

| t | x | $a_{1,0}$ | $a_{1,1}$ | ... | $a_{2,0}$ | $a_{2,1}$ | ... | $a_{\chi,0}$ | $a_{\chi,1}$ | ... | $a_{\chi,n_\chi}$ |
|---|---|---|---|---|---|---|---|---|---|---|---|
| 1 | $x_1$ | 34.5 | 23.1 | ... | 12.3 | 92.5 | ... | 83.6 | 52.4 | ... | 72.5 |
| 2 | $x_2$ | 23.6 | 87.5 | ... | 64.4 | 84.9 | ... | 93.4 | 38.6 | ... | 28.5 |
| ... | ... | ... | ... | | ... | ... | | ... | ... | | ... |
| $i_c$ | $x_{i_c}$ | 76.9 | 82.5 | ... | 93.3 | $a_{j,t,i_c}$ | ... | 37.5 | 82.3 | ... | 84.4 |
| ... | ... | ... | ... | | ... | ... | | ... | ... | | ... |
| $n_c$ | $x_{nc}$ | 61.4 | 90.6 | ... | 72.3 | 26.4 | ... | 83.5 | 26.4 | ... | 28.6 | where $i_c, n_c$ index and dimension of the look-up table ($n_c$ is the number of considered quantized states)

x is the time dependant state vector of the system

Table 17 establishes the relationship between the time dependent state vector of the system, the locomotion related phenomenon and the kinematic and the kinetic variables of the lower extremities joints, which are the following static characteristics:

$$\hat{\theta}_{g,h} = f^\theta(x,x) \qquad \text{Equation 18}$$

$$\hat{m}_{g,h} = f^m(x,x) \qquad \text{Equation 19}$$

The methodology used to identify the parameters $a_{j,i}(x)$ is based on the application of a curve-fitting algorithm to a set of data provided from experimentation on human subjects. This experimentation is performed in a laboratory environment under controlled conditions, yielding a set of data in the form of an array, as shown in Table 16.

The curve-fitting algorithm is used to obtain the parameters $a_{j,i}(x)$ for every given time dependant state vector x. This data is used to construct the look-up table, as shown in Table 17.

Figure 20:
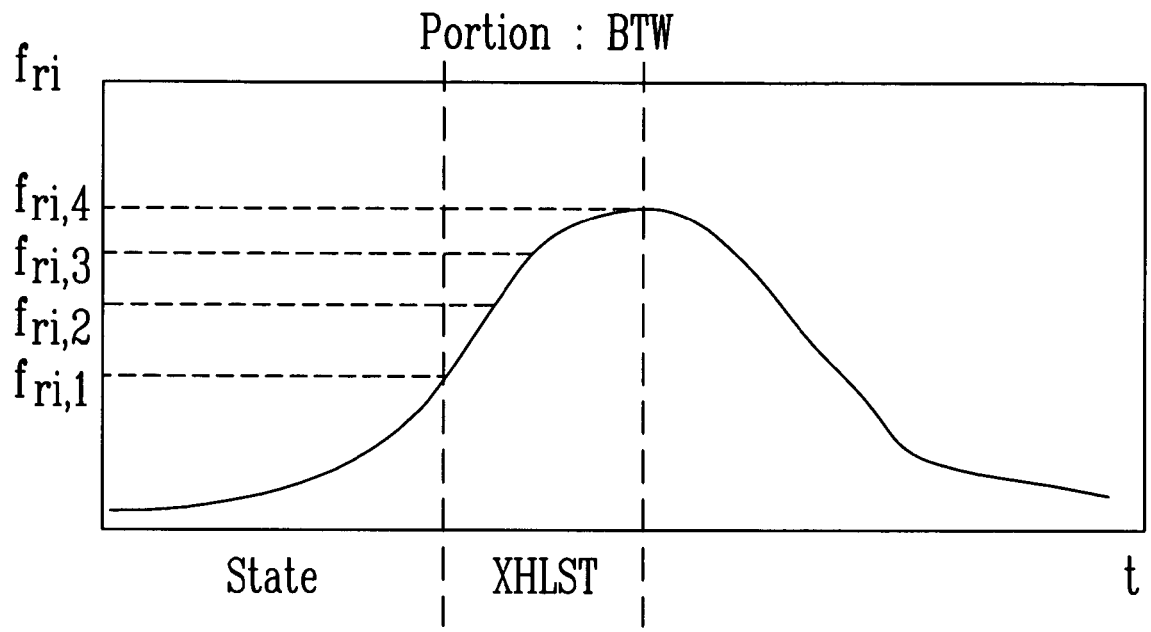
FIG. 20 is a graph showing an example of curve representing a kinematic or kinetic variable for a given portion of locomotion, phase of locomotion portion and subject's speed.
Figure 21:
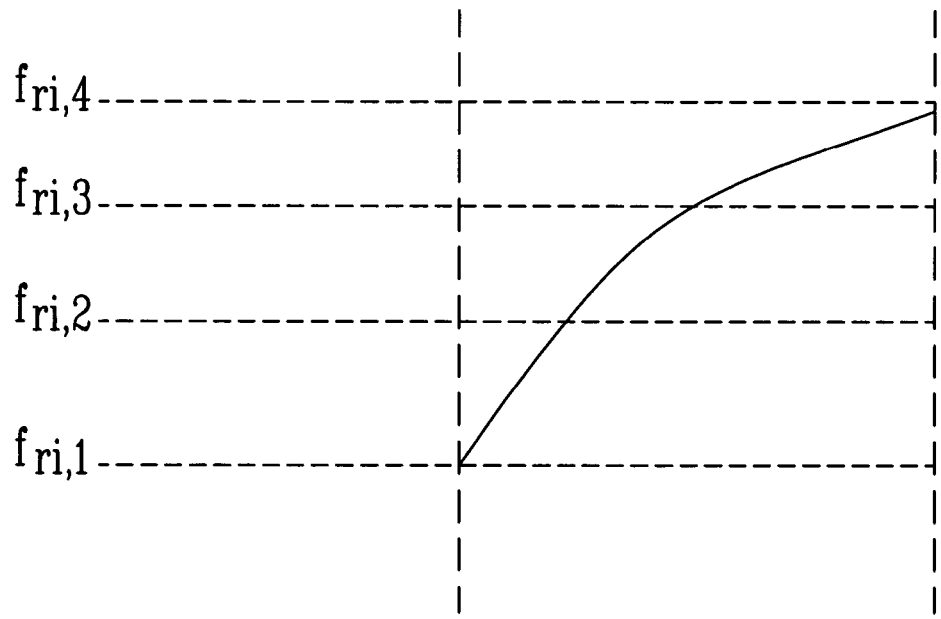
FIG. 21 is an enlarged representation of FIG. 20.

An example of configuration for the method previously described is presented below:

the particularities of this configuration are:
a. the locomotion related phenomenon is composed of a set of four localized plantar pressures supplied by the main artificial proprioceptors;
b. the time dependant state vector is composed of:
 i. the walking speed of the subject;
 ii. the phase of locomotion portion and the portion of locomotion;
 iii. and if Equation 16 and Equation 17 are linear functions:
 iv. the binary formatted magnitude of the four localized plantar pressures;
the family of functions depicting the static characteristics $\hat{\theta}_{g,h} = f^\theta(x, x)$ and $\hat{m}_{g,h} = f^m(x, x)$, as described in Equation 16 and Equation 17;

or a. the family of functions depicting the time-dependant equations $\hat{\theta}_{g,h} = f^{\theta}(x,t)$ and $\hat{m}_{g,h} = f^m(x, t)$, as described in Equation 16 and Equation 17 when $f_{r_{i_f}}$ is substituted by time t.
the selected lower extremities joints is the knee joint, which is the joint between the thigh (th) and the shank (sh);
the selected plan of motion is the sagittal plan;

In the case where Equation 16 and Equation 17 are linear functions, the time dependant state vector further comprises the binary formatted magnitude of the four localized plantar pressures as added parameters to further segment the curve representing the kinematic ($\theta_{g,h}$) or kinetic ($m_{g,h}$) variables. This is due to the fact that, as shown by FIG. 20, that for a given portion of locomotion, phase of locomotion portion and subject's speed, the curve representing the kinematic ($\theta_{g,h}$) or kinetic ($m_{g,h}$) variables cannot efficiently be approximated by a linear function. To that end, the binary formatted plantar pressures are used to further subdivide the phase of locomotion portion in a number of intervals on which the curve representing the kinematic ($\theta_{g,h}$) or kinetic ($m_{g,h}$) variables may be approximated by linear functions. FIG. 21 is a close-up view of FIG. 20 where it is shown that the curve representing the kinematic ($\theta_{g,h}$) or kinetic ($m_{g,h}$) variables appear relatively linear on each of the added subdivisions. Thus, the use of Equation 16 and Equation 17 which are linear functions entails that the time dependant stated vector will further comprise the binary formatted plantar pressures.

It should be noted that in the preferred embodiment, the lookup table contains mathematical relationships that have been normalized in amplitude. The TG (44) uses the relative value of the localized plantar pressures instead of the magnitude of the signal. This means that the localized plantar pressures are set into a [0, 1] scale for a specific state of the whole system $\chi(k)$. This ensures that the mathematical relationships (time-dependant equations and static characteristics) are independent of the weight of the subject. It is worth to note that, because the TG's architecture use the walking speed as a component of the state of the whole system, the static characteristics lookup table is valid for any walking speed comprised within the operational conditions, which are, in the preferred embodiment, between 84 and 126 steps/min, though the lookup table may be computed for other intervals.

The Regulator (48) uses a control law with a similar structure to control algorithms currently employed in numerous commercial or experimental applications. Various control laws may be implemented in the Regulator (48), examples of which are provided below.

First, the Regulator (48) may use a simple PID control law, which is written as:

$$\mu(t) = k_d \dot{\bar{x}}(t) + k_p \bar{x}(t) + k_i \int \bar{x} dt \qquad \text{Equation 20}$$

where
- $k_d$ is the gain associated to the differential component of the regulator
- $k_p$ is the gain associated to the proportional component of the regulator
- $k_i$ is the gain associated to the integral component of the regulator
- $x_i$ is the requested trajectory
- $x_o$ is the trajectory performed by the system
- $\bar{x}$ is the error between the requested ($x_i$) and performed trajectory ($x_o$)
- $\mu$ is the set point intended to the system applied to the proposed system, that is $x=\theta$ or $x=m$, we have:

$$\mu_{g,h}^{\lambda}(t) = k_d \dot{\bar{x}}_{g,h}(t) + k_p \bar{x}_{g,h} + k_i \int \bar{x}_{g,h} dt \qquad \text{Equation 21}$$

where
- g=[sagittal (sg), frontal (fr), transversal (tr)] is the plan of the motion
- h=[hip (hp), knee (kn), ankle (an), metatarsophalangeal (mp)] is the joint
- $x=\theta$ or m where the transfer function between the error x and the set-point is expressed as:

$$\frac{\mu_{g,h}^{\theta}(t)}{\bar{x}_{g,h}(t)} = \frac{b_2 \cdot z^2 + b_1 \cdot z + b_0}{z(z-1)} \qquad \text{Equation 22}$$

where
$b_2 = k_i + k_p + k_d$
$b_1 = -(k_p + k_d)$
$b_0 = k_d$
$x=\theta$ or m in which the corresponding recurrent equation is:

$$\mu_{g,h}^{x}(k) = \mu_{g,h}^{x}(k-1) + b_0 \bar{x}_{g,h}(k-2) + b_1 \bar{x}_{g,h}(k-1) + b_2 \cdot \bar{x}_{g,h}(k) \qquad \text{Equation 23}$$

where
- k is the current increment
- $x=\theta$ or m

Secondly, the Regulator (48) may use an adaptive PID control law. The transfer function of an adaptive PID is the same as that of a conventional PID but the parameters $b_2$, $b_1$ and $b_0$ are function of the state of the whole system $\chi(k)$. From Equation 23, the recurrence equation of the adaptive PID is:

$$\mu_{g,h}^{x}(k) = \mu_{g,h}^{x}(k-1) + b_0(\chi(k)) \cdot \bar{x}_{g,h}(k-2) + b_1(\chi(k)) \cdot \bar{x}_{g,h}(k-1) + b_2(\chi(k)) \cdot \bar{x}_{g,h}(k) \qquad \text{Equation 24}$$

where
- k is the current increment
- $x=\theta$ or m

Thirdly, the Regulator (48) may use a conventional PID with measured moment, which may be written as:

$$f_{g,h}^{\mu}(k) = f_{g,h}^{m}(k) + \bar{f}_{g,h}(k) \qquad \text{Equation 25}$$

where
- $f_{g,h}^{m}(k)$ is the force measured at the joint
- $\bar{f}_{g,h}(k)$ is the force generated by the regulator
- $f_{g,h}^{\mu}(k)$ is the set point of the force intended to the joint Form Equation 22, the transfer function between the position error $\bar{x}_{g,h}$ and the force set-point $\bar{f}_{g,h}(k)$ is expressed as:

$$\frac{\bar{f}_{g,h}(t)}{\bar{x}_{g,h}(t)} = K \cdot \left( \frac{b_2 \cdot z^2 + b_1 \cdot 2 + b_0}{z(z-1)} \right) \qquad \text{Equation 26}$$

where
- K is the gain yielded by the device between the position and the force set point
- $x=\theta$ or m Thus, the recurrent equation of the final force set point $f_{g,h}^\mu(k)$ is given by the following relationship:

$$f_{g,h}^\mu(k) = f^n(k) + \bar{f}_{g,h}(k-1) + b_0 \bar{x}_{g,h}(k-2) + b_1 \bar{x}_{g,h}(k-1) + b_2 \cdot \bar{x}_{g,h}(k) \quad \text{Equation 27}$$

where k is the current increment x=θ or m

What is claimed is:

1. A method for determining a portion of locomotion and a phase of locomotion portion in view of controlling an actuated prosthesis in real time, the method comprising:
   providing a plurality of main artificial proprioceptors;
   receiving a data signal from each of the main artificial proprioceptors;
   obtaining a first and a second derivative signal of at least some of the data signals;
   obtaining a third derivative signal for at least one of the data signals;
   using a set of first state machines to select one state among a plurality of possible states for each main artificial proprioceptor with the corresponding data and derivative signals;
   generating the phase of locomotion portion using the states of the main artificial proprioceptors; and
   using a second state machine to select the portion of locomotion among a plurality of possible portions of locomotion using events associated to the data signals.

2. The method according to claim 1, further comprising:
   pre-processing the data signals before obtaining the derivative signals.

3. The method according to claim 2, wherein the pre-processing comprises:
   filtering the data signals; and
   normalizing the data signals; and
   binary formatting the data signals for adapting them to input specifications of the first state machines.

4. The method according to claim 3, wherein the step of normalizing the data signals comprises:
   converting the data signals using first conversion coefficients obtained during a zero-calibration procedure; and
   converting the data signals using second conversion coefficients obtained during a weight-calibration procedure.

5. The method according to claim 1, wherein the main artificial proprioceptors include plantar pressure sensors, the method comprising:
   sensing the plantar pressure at a plurality of locations, the data signals from the plantar pressure sensors being indicative of the plantar pressure at these locations.

6. The method according to claim 5, further comprising auxiliary artificial proprioceptors, the auxiliary artificial proprioceptors including an angular position sensor provided between two movable parts of the prosthesis, the method comprising:
   generating a data signal indicative of the angular position between the two movable parts, the data signal from the angular position sensor being used in at least one of the events in the second state machine.

7. The method according to claim 5, further comprising auxiliary artificial proprioceptors, the auxiliary artificial proprioceptors including two angular velocity sensors, one being provided on a shank of a non-amputee leg and the other being on a residual limb, the method comprising:
   generating data signals indicative of the angular velocity measured at each angular velocity sensor, the data signals from the angular velocity sensors being used in at least one of the events in the second state machine.

8. The method according to claim 5, wherein the plantar pressure is sensed for at least four locations, two of the locations being at a right foot and two of the locations being at a left foot.

9. The method according to claim 8, wherein one of the locations at the right foot and one at the left foot are at a calcaneus region, another one of the locations at the right foot and one at the left foot are at a metatarsophalangeal region.

10. The method according to claim 9, wherein the right and left plantar pressure sensors are provided in corresponding insoles.

11. The method according to claim 9, wherein one of the feet is an artificial foot, the other being a natural foot.

12. The method according to claim 9, wherein both feet are artificial feet.

13. The method according to claim 9, wherein the step of obtaining the third derivative signal for at least one of the data signals comprises:
   obtaining the third derivative for the data signal indicative of the plantar pressure at the calcaneus region of the right foot; and
   obtaining the third derivative for the data signal indicative of the plantar pressure at the calcaneous region of the left foot.

14. The method according to claim 13, further comprising:
   calculating complementary signals from at least some of the data signals, the states of the main artificial proprioceptors being selected with data, complementary and derivative signals.

15. The method according to claim 14, wherein the step of calculating complementary signals comprises:
   calculating a first complementary signal using the data signals indicative of the plantar pressure at the calcaneus region and at the metatarsophalangeal region of the left foot;
   calculating a second complementary signal using the data signals indicative of the plantar pressure at the calcaneus region and at the metatarsophalangeal region of the right foot;
   calculating a third complementary signal using the data signals indicative of the plantar pressure at the calcaneus region of the right foot and that of the left foot;
   calculating a fourth complementary signal using the data signals indicative of the plantar pressure at the metatarsophalangeal region of the right foot and that of the left foot; and
   calculating a fifth complementary signal using the data signals indicative of the plantar pressure at the calcaneus region of the right foot and that of the left foot, and the metatarsophalangeal region of the right foot and that of the left foot.

16. The method according to claim 1, wherein the step of generating the phase of locomotion portion using the states of the main artificial proprioceptors comprises:
   appending binary labels representing the state of each main artificial proprioceptor to create a binary label representing the phase of locomotion portion.

17. The method according to claim 1, wherein the step of receiving the data signal from each of the main artificial proprioceptors comprises:
   receiving at least some of the data signals from a wireless transmission.

18. A method for controlling an actuated prosthesis in real time, the method comprising:
   providing a plurality of main artificial proprioceptors;
   receiving a data signal from each of the main artificial proprioceptors;
   obtaining a first and a second derivative signal for at least some of the data signals;
   obtaining a third derivative signal for at least one of the data signals;
   using a set of first state machines to select one state among a plurality of possible states for each main artificial proprioceptor with the corresponding data and derivative signals;
   generating a phase of locomotion portion using the states of the main artificial proprioceptors;
   using a second state machine to select the portion of locomotion among a plurality of possible portions of locomotion using events associated to the data signals;
   calculating a locomotion speed value;
   determining coefficient values from a lookup table using the phase of locomotion portion, the portion of locomotion and the locomotion speed value;
   calculating at least one dynamic parameter value of the actuated prosthesis using the coefficient values from the lookup table and at least some of the data signals; and
   converting the dynamic parameter value into an output signal to control the actuated prosthesis.

19. The method according to claim 18, wherein the step of determining coefficient values from the lookup table comprises using the phase of locomotion portion, the portion of locomotion, the locomotion speed value and the data signals, the data signals being in binary format.

20. The method according to claim 18, wherein the actuated prosthesis is an actuated leg prosthesis for above-knee amputees, the step of calculating at least one dynamic parameter value comprising:
   calculating at least one torque value and angular position value.

21. The method according to claim 19, wherein the actuated prosthesis includes an actuator using electric power, the output signal being indicative of the electrical power to be supplied to the actuator.

22. The method according to claim 21, further comprising:
   adjusting the output signal in response to at least one feedback signal received from the prosthesis.

23. The method according to claim 22, wherein there are at least a first and a second feedback signal, the first feedback signal being indicative of a relative angular position measured between two movable parts of a knee joint, and the second feedback signal being indicative of a torque value measured between the two movable parts.

24. The method according to claim 18, further comprising the initial step of:
   processing experimental data to create the lookup table.

25. The method according to claim 18, further comprising:
   pre-processing the data signals before obtaining the derivative signals.

26. The method according to claim 25, wherein the pre-processing comprises:
   filtering the data signals;
   normalizing the data signals; and
   binary formatting the data signals for adapting them to input specifications of the first state machines.

27. The method according to claim 26, wherein the step of normalizing the data signals comprises:
   converting the data signals using first conversion coefficients obtained during a zero-calibration procedure; and
   converting the data signals using second conversion coefficients obtained during a weight-calibration procedure.

28. The method according to claim 18, wherein the main artificial proprioceptors include plantar pressure sensors, the method comprising:
   sensing the plantar pressure at a plurality of locations, the data signals being indicative of the plantar pressure at these locations.

29. The method according to claim 28, further comprising auxiliary artificial proprioceptors, the auxiliary artificial proprioceptors including an angular position sensor provided between two movable parts of the prosthesis, the method comprising:
   generating a data signal indicative of the angular position between the two movable parts, the data signal from the angular position sensor being used in at least one of the events in the second state machine.

30. The method according to claim 28, further comprising auxiliary artificial proprioceptors, the auxiliary artificial proprioceptors including two angular velocity sensors, one being provided on a shank of a non-amputee leg and the other being on a residual limb, the method comprising:
   generating data signals indicative of the angular velocity measured at each angular velocity sensor, the data signals from the angular velocity sensors being used in at least one of the events in the second state machine.

31. The method according to claim 28, wherein the plantar pressure is sensed for at least four locations, two of the locations being at a right foot and two of the locations being at a left foot.

32. The method according to claim 31, wherein one of the locations at the right foot and one of the locations at the left foot are at a calcaneus region, another one of the locations at the right foot and one of the locations at the left foot are at a metatarsophalangeal region.

33. The method according to claim 32, wherein the right and left plantar pressure sensors are provided in corresponding insoles.

34. The method according to claim 32, wherein one of the feet is an artificial foot, the other being a natural foot.

35. The method according to claim 32, wherein both feet are artificial feet.

36. The method according to claim 32, wherein the step of obtaining the third derivative signal for at least one of the data signals comprises:
   obtaining the third derivative for the data signal indicative of the plantar pressure at the calcaneous region of the right foot; and
   obtaining the third derivative for the data signal indicative of the plantar pressure at the calcaneous region of the left foot.

37. The method according to claim 36, further comprising:
   calculating complementary signals from at least some of the data signals, the states of the main artificial proprioceptors being selected with data, complementary and derivative signals.

38. The method according to claim 37, wherein the step of calculating the complementary signals comprises:
- calculating a first complementary signal using the data signals indicative of the plantar pressure at the calcaneus region and at the metatarsophalangeal region of the left foot;
- calculating a second complementary signal using the data signals indicative of the plantar pressure at the calcaneus region and at the metatarsophalangeal region of the right foot;
- calculating a third complementary signal using the data signals indicative of the plantar pressure at the calcaneus region of the right foot and that of the left foot;
- calculating a fourth complementary signal using the data signals indicative of the plantar pressure at the metatarsophalangeal region of the right foot and that of the left foot; and
- calculating a fifth complementary signal using the data signals indicative of the plantar pressure at the calcaneus region of the right foot and that of the left foot, and the metatarsophalangeal region of the right foot and that of the left foot.

39. The method according to claim 18, wherein the step of generating the phase of locomotion portion using the states of the main artificial proprioceptors comprises:
- appending binary labels representing the state of each main artificial proprioceptor to create a binary label representing the phase of locomotion portion.

40. The method according to claim 18, wherein the step of receiving the data signal from each of the main artificial proprioceptors comprises:
- receiving at least some of the data signals from a wireless transmission.

* * * * *